United States Patent [19]

Hiraiwa et al.

[11] Patent Number: 4,948,796

[45] Date of Patent: Aug. 14, 1990

[54] PIPERAZINE DERIVATIVE OR ITS SALT, PROCESS FOR PRODUCING THE SAME AND PHARMACEUTICAL COMPOSITION COMPRISING THE SAME AS ACTIVE INGREDIENT

[75] Inventors: Toru Hiraiwa; Kenji Takeda; Joji Nakano, all of Toyama; Mineichi Sudani, Shinminato; Kunikazu Furuhata, Tokyo; Makoto Takata, Toyama; Hiroyo Kawafuchi, Nakaniikawa; Isao Watanabe, Toyama, all of Japan

[73] Assignee: Toyama Chemical Co., Ltd., Tokyo, Japan

[21] Appl. No.: 316,174

[22] Filed: Feb. 27, 1989

[30] Foreign Application Priority Data

Mar. 3, 1988 [JP] Japan .................................. 63-48741
Feb. 3, 1989 [JP] Japan .................................. 01-25555

[51] Int. Cl.$^5$ ................ A61K 31/495; A61K 31/535; C07D 491/044; C07D 487/00
[52] U.S. Cl. .................... 514/254; 514/232.8; 514/233.5; 514/233.8; 514/234.2; 514/234.5; 514/235.2; 514/235.8; 514/236.2; 514/237.2; 514/248; 514/252; 514/253; 544/121; 544/237; 544/359; 544/360; 544/361; 544/362; 544/363; 544/364; 544/366; 544/367; 544/368; 544/369; 544/370; 544/371; 544/372; 544/373; 544/375; 544/376; 544/377; 544/378; 544/379; 544/381
[58] Field of Search ............... 544/361, 402, 403, 381, 544/121, 237, 359, 360, 361, 362, 363, 364, 366, 367, 368, 369, 370, 371, 372, 373, 375, 376, 377, 378, 379, 380; 514/252, 253, 254, 232.8, 233.5, 233.8, 234.2, 234.5, 235.2, 235.8, 236.2, 237.2, 248, 252, 253, 254

[56] References Cited

U.S. PATENT DOCUMENTS

| 3,409,621 | 11/1968 | Villani ................................ 514/254 |
| 3,496,182 | 2/1970 | Fouché ............................... 544/381 |
| 3,661,909 | 5/1972 | Mastursi et al. .................... 544/381 |
| 3,719,679 | 3/1973 | Boissier et al. ..................... 544/381 |
| 4,144,337 | 3/1979 | Bastian ............................... 544/361 |
| 4,616,023 | 10/1986 | Remy ................................. 514/325 |

FOREIGN PATENT DOCUMENTS

| 0269755 | 6/1988 | European Pat. Off. . |
| 2704934 | 2/1977 | Fed. Rep. of Germany . |
| 2341577 | 9/1977 | France . |
| 7894A1 | 12/1987 | World Int. Prop. O. . |

OTHER PUBLICATIONS

Shepard et al, CA 94-156906b (1981).

*Primary Examiner*—Cecilia Shen
*Attorney, Agent, or Firm*—Oblon, Spivak, McClelland, Maier & Neustadt

[57] ABSTRACT

A piperazine derivative represented by the following formula or a salt thereof:

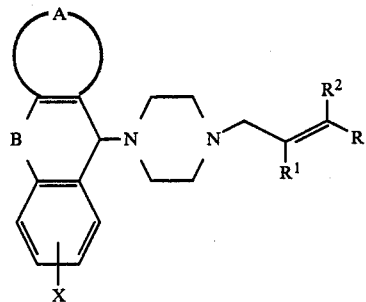

which is useful for curing cerebro-vascular disease and post-cerebro-vascular disease.

25 Claims, No Drawings

PIPERAZINE DERIVATIVE OR ITS SALT, PROCESS FOR PRODUCING THE SAME AND PHARMACEUTICAL COMPOSITION COMPRISING THE SAME AS ACTIVE INGREDIENT

This invention relates to a novel piperazine derivative or a salt thereof, a process for producing the same, a pharmaceutical composition comprising the same as an active ingredient and a curing method comprising applying the composition.

Heretofore, cerebro-vasodilators such as cinnarizine, flunarizine, cinepazide maleate, ifenprodil tartrate, vinpocetine and the like have been clinically used for the purpose of curing cerebro-vascular disease and post-cerebro-vascular disease.

However, it cannot be said that these are sufficient in selectivity to cerebral blood vessel though they have a vasodilation activity. Accordingly, it has been desired to develop chemically stable compounds which can selectively dilate cerebral blood vessels and have an activity to protect cerebral cells from ischemic invasion.

Under such circumstances, the inventors of this invention have made extensive research on such compounds to find that piperazine compounds having groups represented by the following formulas at the 1- and 4-positions of piperazine ring, respectively:

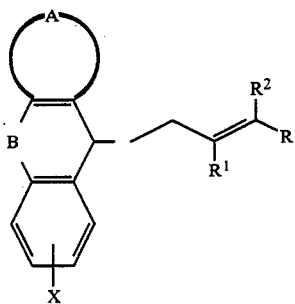

wherein A, B, R, $R^1$, $R^2$ and X are as will be defined hereinafter, that is, novel piperazine derivatives and their salts have not only vasodilation activity excellent in selectivity to cerebral blood vessel but also a cerebral cell-protecting activity and also are chemically stable and very useful as medicines for curing cerebro-vascular disease and post-cerebro-vascular disease.

An object of this invention is to provide a novel piperazine derivative or a salt thereof.

Another object of this invention is to provide a process for producing a novel piperazine derivative or a salt thereof.

A further object of this invention is to provide a pharmaceutical composition comprising the above piperazine derivative or a salt thereof as an active ingredient.

A still further object of this invention is to provide a method of curing cerebro-vascular disease and post-cerebro-vascular disease by applying the above piperazine derivative or a salt thereof.

Other objects and advantages of this invention will become apparent from the following description.

According to this invention, there is provided a piperazine derivative represented by the formula [I] or a salt thereof:

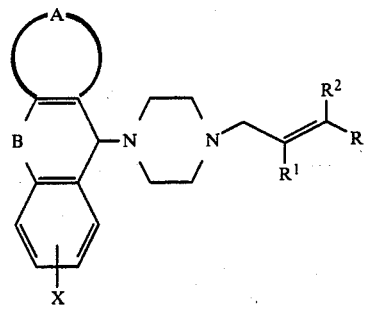

[I]

wherein A and the two carbon atoms to which A attaches form a pyridine ring or form a benzene ring substituted by a nitro group, X represents a hydrogen atom, a halogen atom, a lower alkyl group, a protected or unprotected hydroxyl group, a lower alkoxy group, a protected or unprotected amino group or a nitro group, B represents a group of the formula —$CH_2CH_2$— or —CH=CH— or a group of the formula —$CH_2O$— or —$CH_2S$—, either of which can be in either orientation, $R^1$ represents a hydrogen atom, a halogen atom, a nitro group or a lower alkyl group, $R^2$ represents a hydrogen atom, a halogen atom or a lower alkyl group, R represents an aryl or heterocyclic group which may be substituted by at least one substituent selected from the group consisting of a halogen atom, a protected or unprotected hydroxyl group, a nitro group, a protected or unprotected amino group, a di-(lower alkyl)amino group, a protected or unprotected carboxyl group, a cyano group, a lower alkenyl group, a lower acyl group, an aryl group, a lower alkenyloxy group, an aryloxy group, a heterocyclic group, a heterocyclicoxy group, a lower alkoxy group, a lower alkylthio group, a lower alkylsulfinyl group, a lower alkylsulfonyl group, a lower alkylsulfonylamino group, a lower alkylenedioxy group, a substituted or unsubstituted carbamoyl or sulfamoyl group or a substituted or unsubstituted lower alkyl group.

This invention further provides a process for producing the above compound, a pharmaceutical composition comprising the compound as an active ingredient and a method of curing a cerebro-vascular disease and post-cerebro-vascular disease by applying the composition.

In the present specification, unless otherwise specified, the term "halogen atom" includes fluorine atom, chlorine atom, bromine atom, iodine atom and the like; the term "lower alkyl group" means a $C_{1-6}$alkyl group such as methyl, ethyl, n-propyl, isopropyl, n-butyl, isobutyl, t-butyl, pentyl, hexyl or the like; the term "lower alkoxy group" means a $C_{1-6}$alkyl—O— group; the term "lower alkenyl group" means a $C_{2-6}$alkenyl group such as vinyl, propenyl and the like; the term "lower alkenyloxy group" means a $C_{2-6}$alkenyl—O— group; the term "lower alkylthio group" means a $C_{1-6}$alkyl—S— group; the term "lower alkylsulfinyl group" means a $C_{1-6}$alkyl—SO— group; the term "lower alkylsulfonyl group" means a $C_{1-6}$alkyl—$SO_2$— group; the term "lower alkylsulfonylamino group" means a $C_{1-6}$alkyl—$SO_2NH$— group; the term "lower alkoxycarbonyl group" means a $C_{1-6}$alkyl—O—CO— group; the term "lower alkoxycarbonyloxy group" means a $C_{1-6}$alkyl—O—CO—O— group; the term "di-(lower alkyl)amino group" means a di-($c_{1-6}$alkyl)amino group; the term "aryl group" includes phenyl, naphthyl and the like; the term "aryloxy group" includes phenyloxy, naphthyloxy and the like; the term "heterocyclic group" means a 5- or 6-membered heterocyclic group having at least one hetero atom selected from the group consisting of nitrogen, oxygen and sulfur atoms such as an unsubstituted or oxo group-substituted pyrrolidinyl or morpholinyl group, thienyl, furyl, pyrrolyl, thiazolyl, oxazolyl, thiadiazolyl, oxadiazolyl, imidazolyl, pyridyl or the like or a fused heterocyclic group such as benzothienyl, benzofuranyl, indolyl, benzimidazolyl, benzotriazolyl, benzothiazolyl, benzoxazolyl, benzothiazolyl, benzoxadiazolyl, quinolyl, phthalazyl, benzdioxanyl or the like; the term "hererocyclicoxy group" means a heterocyclic—O— group; the term "lower acyl group" means a $C_{1-6}$acyl group such as formyl, acetyl, butyryl or the like and the term "lower alkylenedioxy group" means a $C_{1-4}$alkylenedioxy group such as methylenedioxy, ethylenedioxy or the like.

In the definition of R, the substituent for the substituted or unsubstituted carbamoyl or sulfamoyl group includes lower alkyl groups. Further, the substituent for the substituted or unsubstituted lower alkyl group includes halogen atoms, protected or unprotected hydroxyl groups, a cyano group, protected or unprotected amino groups, a carbamoyl group, protected or unprotected carboxyl groups, lower alkoxy groups, lower alkoxycarbonyl groups, aryl groups and heterocyclic groups. The substituted lower alkyl group may have at least one of these substituents.

The protective group for the hydroxyl, amino and carboxyl groups include, for example, conventional protective groups for hydroxyl, amino and carboxyl groups as mentioned in, for example, Theodra W. Green, Protective Groups in Organic Synthesis (1981) published by John Wiley & Sons, Inc. and the like.

The salt of the piperazine derivative of the formula [I] may be any pharmaceutically acceptable salt, and includes salts with organic and inorganic acids, for example, salts with mineral acids such as hydrochloric acid, hydrobromic acid, sulfuric acid, phosphoric acid and the like; salts with carboxylic acids such as formic acid, acetic acid, fumaric acid, maleic acid, malic acid, tartaric acid, aspargic acid and the like; salts with sulfonic acids such as methanesulfonic acid, benzenesulfonic acid, toluenesulfonic acid, hydroxybenzenesulfonic acid, naphthalenesulfonic acid and the like; etc.

When the piperazine derivative of the formula [I] has isomers, for example, optical isomers, geometrical isomers, tautomeric isomers and the like, this invention covers these isomers and also hydrates, solvates and all crystal forms.

Next, an explanation is made of processes for producing the piperazine derivatives of the formula [I] and their salts.

The piperazine derivative of the formula [I] or a salt thereof can be produced in a manner known per se, for example, by the following production processes:

Production Process 1

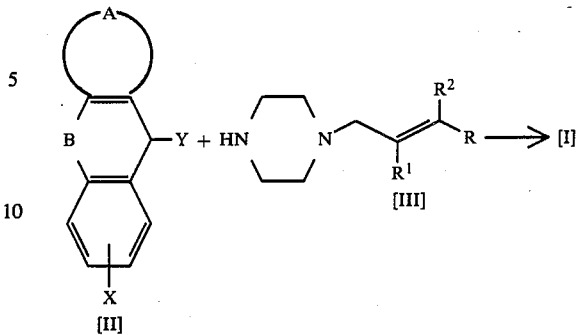

Production Process 2

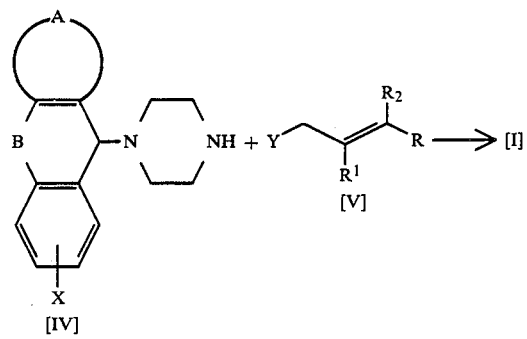

Production Process 3

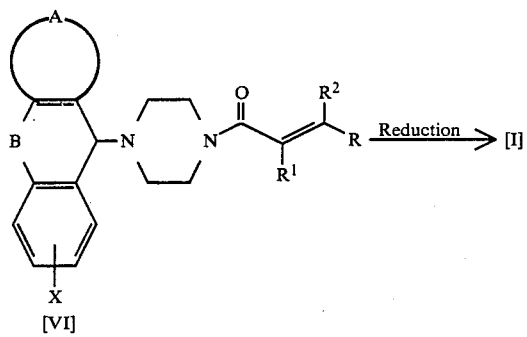

In the above formulas, A, B, $R^1$, $R^2$, R and X have the same meanings as defined above, and Y represents a removable group.

The removal group which Y represents includes, for example, $C_{1-6}$alkylsulfonyloxy groups such as methylsulfonyloxy, ethylsulfonyloxy and the like; arylsulfonyloxy groups such as phenylsulfonyloxy, tolylsulfonyloxy and the like and halogen atoms.

The production processes indicated by reaction formulas above are explained in more detail below.

Production Process 1

The piperazine derivative of the formula [I] or a salt thereof can be obtained by reacting a compound of the formula [II] with a compound of the formula [III] in the presence or absence of a solvent and a base.

The solvent used in the above reaction may be any solvent as far as it does not adversely affect the reaction, and includes, for example, alcohols such as methanol, ethanol, propanol, butanol, ethylene glycol, ethylene glycol monomethyl ether and the like; aromatic hydrocarbons such as benzene, toluene and the like; halogenated hydrocarbons such as methylene chloride, chloroform, 1,2-dichloroethane and the like; ethers such as tetrahydrofuran, dioxane, 1,2-dimethoxyethane and the like; esters such as ethyl acetate, butyl acetate and the like; nitriles such as acetonitrile and the like; amides such as N,N-dimethylformamide, N,N-dimethylacetamide, N-methylpyrrolidone and the like; water; etc. These solvents may be used alone or in admixture of two or more.

The base used in the above reaction includes, for example, tertiary amines such as triethylamine, N-methylmorpholine, N,N-dimethylaniline, 4-(N,N-dimethylamino)pyridine and the like; inorganic bases such as sodium hydroxide, potassium hydroxide, sodium carbonate, potassium carbonate and the like; etc.

In the above reaction, the amounts of the compounds of the formula [II] and the base used are each 0.5 to 3.0 moles per mole of the compound of the formula [III].

The above reaction may usually be carried out at a temperature of 0° to 100° C. for a period of 10 minutes to 24 hours.

Production Process 2

The piperazine derivative of the formula [I] or a salt thereof can also be produced by reacting a compound of the formula [IV] with a compound of the formula [V] in the presence or absence of a solvent and a base.

The solvent and the base used in the above reaction include those mentioned in Production Process 1.

In the above reaction, the amounts of the compound of the formula [IV] and the base used are each 0.5 to 3.0 moles per mole of the compound of the formula [V].

The above reaction may usually be carried out at a temperature of 0° to 100° C. for a period of 10 minutes to 24 hours.

Production Process 3

The piperzaine derivative of the formula [I] or a salt thereof can also be produced by reducing a compound of the formula [VI].

This reaction is usually carried out in an organic solvent, and the organic solvent includes, for example, aliphatic hydrocarbons such as petroleum ether, hexane and the like; aromatic hydrocarbons such as benzene, toluene and the like; ethers such as dimethyl ether, diethyl ether, tetrahydrofuran, dioxane, 1,2-dimethoxyethane and the like; organic acids such as acetic acid, trifluoroacetic acid and the like; and alcohols such as methanol, ethanol, isopropanol and the like. The above solvents may be used alone or in admixture of two or more.

The reducing agent used in the above reaction includes, for example, lithium aluminum hydride, sodium bis(2-methoxyethoxy)aluminum hydride, sodium borohydride, aluminum hydride, diborane, etc.

In the above reaction, the amount of the reducing agent is 0.5 to 10.0 moles per mole of the compound of the formula [VI].

The above reaction may usually be carried out at a temperature of −20° to 100° C. for a period of 10 minutes to 12 hours.

The compounds of the formulas [II], [III], [IV] and [V] may be used in the form of a salt. These salts include the same salts as mentioned as to the salts of the piperazine derivatives of the formula [I].

When the compounds of the formulas [II], [III], [IV], [V] and [VI] have an amino, hydroxyl or carboxyl group, the group may previously be protected with a conventional protective group and after the reaction, the conventional protective group may be removed in a manner known per se.

When the compounds of the formulas [II], [III], [IV], [V] and [VI] have isomers such as optical isomers, geometrical isomers, tautomeric isomers and the like, these isomers may be used instead of the respective compounds. Also, the compounds may be used in the form of a hydrate, a solvate or a crystal.

The compounds of the formulas [II], [III], [IV], [V] and [VI] which are the starting materials for producing the compound of this invention can be produced by, for example, the following methods or a combination of methods known per se.

(1) Method for preparing the compound of the formula [II] or [IV]

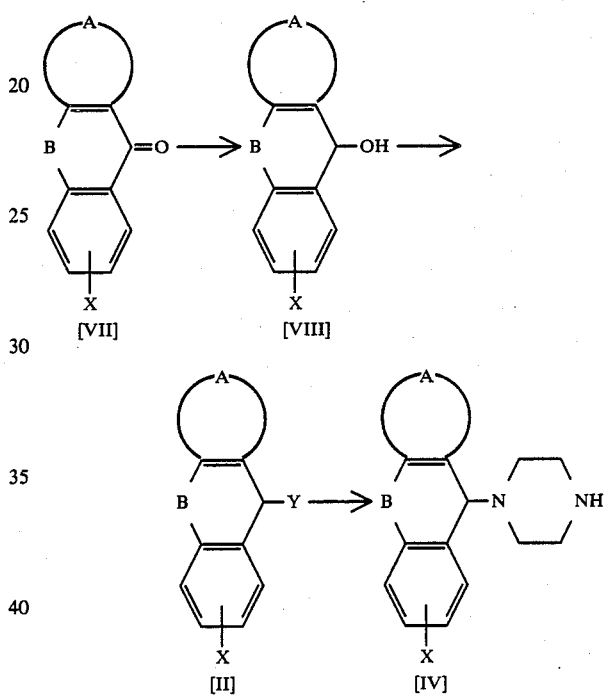

wherein A, B, X and Y have the same meanings as defined above.

The compound of the formula [VII] can be prepared by, for example, the method described in Japanese Patent Application Kokoku (Publication) No. 14,788/70, Japanese Patent Application Kokai (Laid-Open) No. 41/86 or the like or another method known per se.

The compound of the formula [VIII] can be prepared by subjecting the compound of the formula [VII] to reduction with a reducing agent such as sodium borohydride, lithium aluminum hydride, aluminum hydride, diborane or the like.

The compound of the formula [II] can be prepared by subjecting, for example, a compound of the formula [VIII] to conventional halogenation with a halogenating agent such as thionyl chloride, thionyl bromide, phosphorus tribromide or the like; a hydrogen halide such as hydrogen chloride, hydrogen bromide or the like; or a combination of carbon tetrabromide with triphenylphosphine, or alternatively to sulfonylation with methanesulfonyl chloride or toluenesulfonyl chloride.

The compound of the formula [II] thus obtained can be used without isolation in the subsequent reaction.

The compound of the formula [IV] can be prepared by reacting the compound of the formula [II] with piperazine in the same manner as in Production Process 1 or 2 described above.

The compounds of the formulas [II], [IV], [VII] and [VIII] can also be used in the form of a salt. The salts include the same salts as mentioned as to the salt of the piperazine derivative of the formula [I].

The compounds of the formulas [VII], [VIII] and [II] in which X is a hydroxyl or amino group can previously be subjected to protection of the hydroxyl or amino group with a conventional protective group and, after the reaction, the protective group can be removed in a manner known per se.

(2) Method for preparing the compound of the formula [III], [V] or [VI]

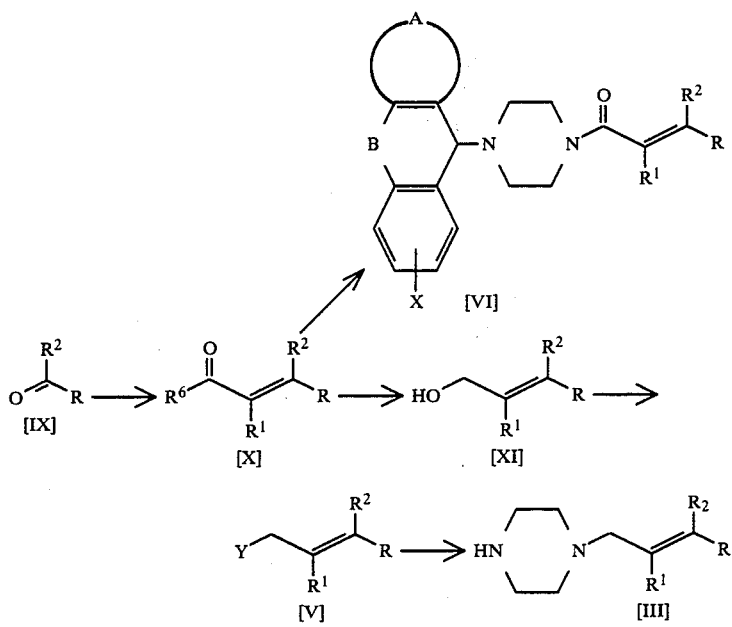

wherein A, B, $R^1$, $R^2$, R, X and Y have the same meanings as defined above and $R^6$ represents a hydrogen atom, a halogen atom, a hydroxyl group, a lower alkoxy group or a lower alkoxycarbonyloxy group.

The compound of the formula [IX] can be prepared by, for example, the method disclosed in Journal of Chemical Society of Japan, vol. 86, No. 8, pp. 860–863 (1965) or another method known per se.

The compound of the formula [X] in which $R^6$ is a hydrogen atom can be prepared by subjecting a compound of the formula [IX] and acetaldehyde to the Claisen-Schmitt condensation.

The compound of the formula [X] in which $R^6$ is a hydroxyl group can be prepared by subjecting a compound of the formula [IX] and malonic acid to the Knoevenagel condensation.

The compound of the formula [X] in which $R^6$ is a halogen atom can be prepared by reacting the compound of the formula [X] in which $R^6$ is a hydroxyl group with a halogenating agent such as thionyl chloride, thionyl bromide, oxalyl chloride, phosphorus oxychloride or the like.

The compound of the formula [X] in which $R^6$ is a lower alkoxy group can be prepared by subjecting, for example, the compound of the formula [IX] to conventional Wittig reaction. The Wittig reagent to be used in the Wittig reaction includes a sodium or lithium derivative of a dialkyl phosphonate represented by the formula [XII]:

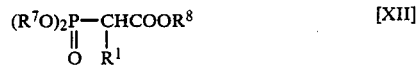

wherein $R^1$ has the same meaning as defined above and $R^7$ and $R^8$, which may be the same or different, represent lower alkyl groups, (prepared by reacting a dialkyl phosphonate with sodium hydride or lithium bromide and triethylamine) and a phosphorane compound represented by the formula [XIII]:

wherein $R^1$ and $R^8$ have the same meanings as defined above.

The compound of the formula [X] in which $R^6$ is a lower alkoxycarbonyloxy group can be prepared by reacting the compound of the formula [X] in which $R^6$ is a hydroxyl group with a lower alkoxycarbonyl chloride.

The compound of the formula [X] obtained can be used without isolation in the subsequent reaction.

The compound of the formula [XI] can be prepared by subjecting the compound of the formula [X] to conventional reduction with a reducing agent such as sodium borohydride, lithium aluminum hydride, diisobutylaluminum hydride or the like.

The compound of the formula [V] can be prepared by subjecting the compound of the formula [XI] to conventional halogenation with a halogenating agent such as thionyl chloride, thionyl bromide, phosphorus tribromide or the like or a combination of triphenylphosphine and carbon tetrabromide or to halogenation or sulfonylation with methanesulfonyl chloride or toluenesulfonyl chloride.

The compound of the formula [V] obtained can be used without isolation in the subsequent reaction.

The compound of the formula [III] can be prepared by reacting the compound of the formula [V] with piperazine in the same manner as in Production Process 1 or 2.

The compound of the formula [VI] can be prepared by reacting the compound of the formula [X] with the compound of the formula [IV] in the presence or absence of a dehydrating agent, such as N,N'-dicyclohexylcarbodiimide, diethylphosphoryl acid cyanide or the like or in the same manner as in Production Process 1 or 2.

The compounds of the formulas [IX], [X], [XI], [V], [VI] and [III] in which R is a phenyl group substituted by a hydroxyl, amino or carboxyl group can be previously subjected to protection of the hydroxyl, amino or carboxyl group with a conventional protective group and, after the reaction, the conventional protective group can be removed in a manner known per se.

The piperazine derivative of the formula [I] or a salt thereof thus obtained can be isolated and purified by a conventional method such as extraction, crystallization, column chromatography or the like.

The piperazine derivative of the formula [I] or a salt thereof can be converted into another piperazine derivative of the formula [I] or a salt thereof by a combination of means known per se such as oxidation, reduction, condensation, substitution, dehydration, hydrolysis and the like.

When the compound of this invention is used as a medicine, the compound can be orally or parenterally administered as it is or in admixture with an additive such as a pharmaceutically acceptable excipient, carrier or diluent in the form of tablets, capsules, granules, fine granules, powder or injection. The dosage of the compound, when administered orally, is usually about 10 to 600 mg per adult a day, and this amount is administered at one time or in several portions, and may be varied depending upon the age, weight and symptom of a patient.

Next, the pharmacological activity of typical compounds of this invention is explained in detail below. The compounds of this invention shown in Table 1 where subjected to the following test in the form of a hydrochloride to obtain the results shown in each test item.

TABLE 1

Test compounds

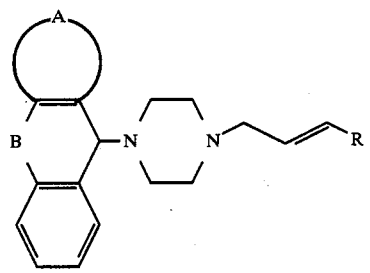

| No. | A | B<br>〈<br>\ | R |
|-----|---|---|---|
| 1 | N=CH—CH=CH |  | 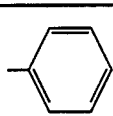 |
| 2 | CH=N—CH=CH | " | 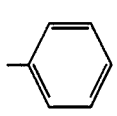 |
| 3 | N=CH—CH=CH | " | 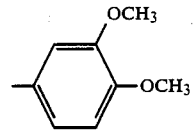 |
| 4 | " | " | 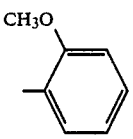 |
| 5 | " | " | 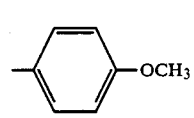 |

TABLE 1-continued
Test compounds
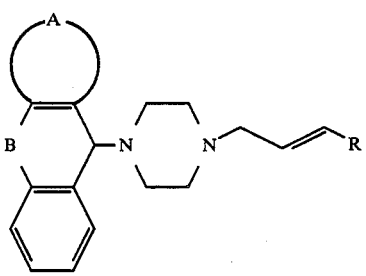
| No. | A | B | R |
|---|---|---|---|
| 6 | " | " | 4-NO₂-phenyl |
| 7 | " | " | 3-phenoxy-4-methoxyphenyl |
| 8 | " | " | 2,3,4-trimethoxyphenyl |
| 9 | " | " | 3,4-methylenedioxyphenyl (ethylenedioxy) |
| 10 | " | " | 3-NO₂-4-OCH₃-phenyl |
| 11 | " | " | 3-Cl-phenyl |
| 12 | " | " | 3,4-diCl-phenyl |
| 13 | " | " | 3,4-diF-phenyl |

TABLE 1-continued
Test compounds
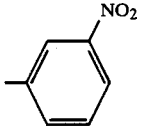
| No. | A | B | R |
|---|---|---|---|
| 14 | " | " | 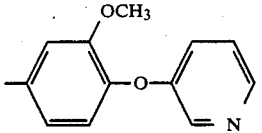 |
| 15 | " | " | 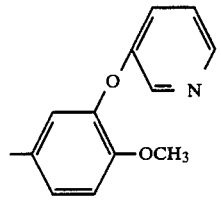 |
| 16 | " | " | 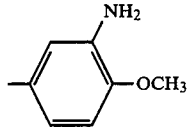 |
| 17 | " | " | 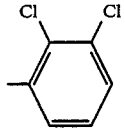 |
| 18 | " | " | 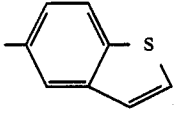 |
| 19 | " | " | 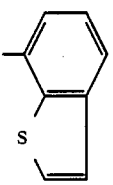 |
| 20 | " | " |  |

TABLE 1-continued
Test compounds

| No. | A | B | R |
|-----|---|---|---|
| 21 | " | " | 5-nitronaphthalen-1-yl |
| 22 | " | cyclopropyl | phenyl |
| 23 | CH=CH—C(NO₂)=CH | cyclobutyl | phenyl |
| 24 | " | " | 2-methoxyphenyl |
| 25 | " | thiophen-2-yl | phenyl |
| 26 | " | cyclobutyl | 3-nitrophenyl |

Control compound A: Flunarizine dihydrochloride

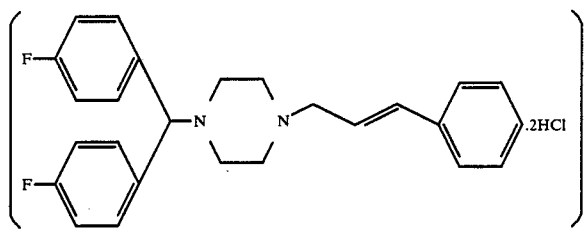

1. Vertebral Blood Flow Increasing Activity

Mongrel dogs of both sexes weighing from 12 to 20 kg were anesthetized with sodium pentobarbital. Vertebral blood flow (VBF) and femoral blood flow (FBF) were measured by an electromagnetic flowmeter (MFV-2100 and MFV-3100, Nihon Kohden).

Test compound solutions were injected intravenously in a volume of 0.2 ml/kg.

The increased rate of VBF by 1 mg/kg of papaverine hydrochloride was regarded as 100%, and 50% effective doses ($ED_{50}$) of test compounds were determined.

Also, the ratio of percent increase of VBF to FBF elicited by test compounds were indicated as an index of cerebral vessel selectivity.

The test compounds were dissolved in a physiological saline solution.

However, each of the test compounds Nos. 7, 23, 24, 25 and 26 was dissolved in an aqueous solution containing 10% of dimethylsulfoxide and 10% of Cremophor EL (Sigma) at a concentration of 15 mg/ml and the control compound A (flunarizine) was dissolved in an aqueous solution containing 20% of dimethylsulfoxide and 20% of Cremophor EL at a concentration of 15 mg/ml. Thereafter, the resulting solution was diluted with a physiological saline solution to the desired concentration. Each study was carried out using 2-5 dogs per group.

The results obtained are shown in Table 2.

TABLE 2

| Test compound No. | VBF $ED_{50}$ (mg/kg) | Cerebral vessel selectivity |
| --- | --- | --- |
| 2 | 0.34 | 8.8 |
| 3 | 0.30 | 5.0 |
| 4 | 0.22 | 3.0 |
| 5 | 0.30 | 8.8 |
| 7 | 0.11 | 16.7 |
| 8 | 0.14 | 4.5 |
| 9 | 0.45 | 6.9 |
| 10 | 0.17 | 9.1 |
| 12 | 0.30 | 5.6 |
| 14 | 0.30 | 3.8 |
| 15 | 0.18 | 4.6 |
| 16 | 0.15 | 3.6 |
| 18 | 0.30 | 10.4 |
| 19 | 0.32 | 4.1 |
| 20 | 0.36 | 4.1 |
| 21 | 0.33 | 3.4 |
| 22 | 0.15 | 5.4 |
| 23 | 0.32 | 5.0 |
| 24 | 0.35 | 14.3 |
| 25 | 0.28 | 10.6 |
| 26 | 0.28 | 4.4 |
| Control compd. A | 0.28 | 2.1 |

2. Protective Effect against Hypobaric Hypoxia

According to the method described by Nakanishi et al., [Life Sci. Vol. 13, 467-474 (1973)], male ICR mice, weighing 20 to 25 g, were placed inside a closed chamber and the inside pressure was rapidly reduced to 210 mmHg.

Each mouse was given 80 mg/kg of test compound orally one or two hours before the mice were placed under the hypobaric condition, and the survival time was measured.

The test compounds were dissolved in a physiological saline solution. However, the test compounds Nos. 7 and 23 were dissolved in an aqueous solution containing 5% of dimethylsulfoxide and 5% of Cremophor EL, and the control compound A (flunarizine) was dissolved in a 1.5% aqueous tartaric acid solution and then they were administered. Each study was carried out using 20 mice per group.

The protective effect against hypobaric hypoxide was determined as a ratio of the survival time of the group to which the test compounds was administered to that of the group to which an aqueous solution containing 5% of dimethylsulfoxide and 5% of Cremophor EL, the latter being indicated as 100.

The results obtained are shown in Table 3.

TABLE 3

| Test compd. No. | 1 | 3 | 6 | 7 | 9 | 11 | 12 | 13 | 14 | 17 | 19 | 20 | 23 | A (control) |
| --- | --- | --- | --- | --- | --- | --- | --- | --- | --- | --- | --- | --- | --- | --- |
| Survival time (ratio) | 180 | 136 | 135 | 158 | 155 | 146 | 129 | 148 | 139 | 143 | 138 | 142 | 205 | 61 |

3. Acute Toxicity

A test compounds were intravenously administered to a group of three male ICR mice, weighing 20 to 26 g. The mortality was determined.

The test compounds were dissolved in a physiological saline solution. However, the test compound Nos. 7, 23 and 24 were dissolved in an aqueous solution containing 10% of dimethylsulfoxide and 10% of Cremophor EL and flunarizine was dissolved in 0.1M aqueous lactic acid solution.

As a result, it was confirmed that concerning the test compounds Nos. 1, 3, 6, 7, 8, 10, 11, 12, 13, 14, 17, 18, 19, 20, 21, 23 and 24 and flunarizine, no death case was found at 25 mg/kg.

From the above results, it can be seen that the compound of this invention has not only excellent cerebral vessel selectivity and protective effect against cerebral hypoxia but also low toxicity.

As mentioned above, the compound of this invention is a very useful compound as a medicine for curing cerebro-vascular disease and post-cerebro-vascular disease.

This invention is explained in more detail referring to Reference Examples, Examples and Preparation Examples. However, this invention is not restricted to these Examples.

In the Examples, the mixing ratio of mixed solvent is by volume in all cases. As the carrier in column chromatography, there was used a silica gel (Kieselgel 60, Art. 7734 manufactured by Merck Co.).

The following abbreviations are used in the Examples:

Me: Methyl
Et: Ethyl
i-Pr: Isopropyl
Ac: Acetyl
IPA: Isopropyl alcohol
IPE: Diisopropyl ether
t-Bu: tert-Butyl
EtOH: Ethanol
AcOEt: Ethyl acetate
THF: Tetrahydrofuran
Ph: Phenyl
Tri: Triphenylmethyl
Si≷: tert-Butyldimethylsilyl In Tables and description sentences, the materials shown in parentheses ( ) refer to solvents used for recrystallization.

REFERENCE EXAMPLE 1

(1) A mixture consisting of 15.1 g of methyl 2-methylnicotinate, 36.0 g of 4-methylbenzaldehyde and 15.0 g of anhydrous zinc chloride was stirred for 30 minutes at 180° C. The resulting reaction mixture was cooled to room temperature. Thereto were added 151 ml of a 10% aqueous sodium hydroxide solution and 100 ml of toluene. The resulting mixture was stirred. The insolubles were removed by filtration. An aqueous layer was separated, washed with toluene and then adjusted to pH 5.0 with acetic acid. The resulting crystals were collected by filtration and dried to obtain 13.2 g of 2-(p-methylstyryl)nicotinic acid. It was recrystallized from ethanol to obtain 10.6 g of colorless crystals having a melting point of 208°–209° C.

IR (KBr) cm$^{-1}$: 2380, 1625, 1560, 1420, 1260, 1140, 965, 800.

(2) 9.56 g of 2-(p-methylstyryl)nicotinic acid was dissolved in 190 ml of ethanol and 3.3 ml of concentrated hydrochloric acid. To the solution was added 1.00 g of 5% palladium-carbon (catalyst), and the mixture was subjected to hydrogenation at 40° C. at atmospheric pressure. The reaction mixture was filtered to remove the catalyst, and the filtrate was subjected to distillation under reduced pressure to remove the solvent. To the resulting residue was added 100 ml of water and the mixture was adjusted to pH 5.0 with a 10% aqueous sodium hydroxide solution. The resulting crystals were collected by filtration and dried to obtain 8.58 g of 2-(p-methylphenethyl)nicotinic acid. It was recrystallized from ethanol to obtain 7.72 g of colorless crystals having a melting point of 172°–173° C.

IR (KBr) cm$^{-1}$: 2350, 1580, 1250, 1140, 1080, 770.

(3) A mixture consisting of 7.23 g of 2-(p-methylphenethyl)nicotinic acid and 94.00 g of polyphosphoric acid was stirred for 1 hour at 140° C. The reaction mixture was poured into 94 ml of concentrated ammonia water with ice-cooling. To the resulting mixture was added carbon tetrachloride, and the organic layer was separated and dried over anhydrous magnesium sulfate. The solvent was removed by distillation under reduced pressure to obtain 5.95 g of brown oily 7-methyl-10,11-dihydro-5H-benzo[4,5]cyclohepta[1,2-b]pyridin-5-one.

IR (neat) cm$^{-1}$: 3020, 2910, 1640, 1600, 1575, 1435, 1290.

The following compound was obtained in a similar manner.

7-Chloro-5H-benzo[4,5]cyclohepta[1,2-b]-pyridin-5-one: Melting point: 140°–142° C. (AcOEt) IR (KBr) cm$^{-1}$: 1620, 1570, 1310, 1285, 840, 800.

REFERENCE EXAMPLE 2

(1) 6.06 g of thiophenol was dissolved in 50 ml of N,N-dimethylformamide. To the solution was added 3.09 g of potassium hydroxide. The resulting mixture was stirred for 1 hour at room temperature. To the reaction mixture was added 8.96 g of 6-nitrophthalide. The mixture was stirred for 2 hours at 50° C. The resulting reaction mixture was mixed with 100 ml of water, and the mixture was adjusted to pH 2 with dilute hydrochloric acid and then extracted with ethyl acetate. The extract was washed with water and a saturated aqueous sodium chloride solution in this order and then dried over anhydrous magnesium sulfate. The solvent was removed by distillation under reduced pressure. The residue was purified by a column chromatography (eluant: chloroform/methanol=30/1) to obtain 7.20 g of yellow crystals of 5-nitro-2-phenylthiomethylbenzoic acid having a melting point of 132°–136° C.

IR (KBr) cm$^{-1}$: 2800, 1680, 1600, 1520, 1340.

(2) 7.0 g of 5-nitro-2-phenylthiomethylbenzoic acid was dissolved in 70 ml of chlorobenzene. 70 g of polyphosphoric acid was added to the solution. The resulting mixture was stirred for 2 hours at 125° C. The reaction mixture was poured into 200 ml of ice water, and the resulting mixture was extracted with ethyl acetate. The extract was washed with a 5% aqueous sodium hydroxide solution, water and a saturated aqueous sodium chloride solution in this order and then dried over anhydrous magnesium sulfate. The solvent was removed by distillation under reduced pressure. The residue was purified by a column chromatography (eluant: chloroform) to obtain 2.5 g of yellow crystals of 9-nitro-6,11-dihydrodibenzo[b,e]thiepin-11-one having a melting point of 154°–157° C.

IR (KBr) cm$^{-1}$: 1630, 1580, 1510, 1340, 1260.

REFERENCE EXAMPLE 3

4.14 g of 5H-benzo[4,5]cyclohepta[1,2-b]-pyridin-5-one was added to 20.7 ml of fuming nitric acid with ice-cooling. The mixture was stirred for 1 hour at room temperature. The reaction mixture was poured into 100 ml of ice water. The resulting mixture was neutralized with potassium carbonate and then extracted with chloroform. The extract was washed with water and dried over anhydrous magnesium sulfate. The solvent was removed by distillation under reduced pressure. The residue was recrystallized from chloroform to obtain 1.90 g of yellow crystals of 7-nitro-5H-benzo[4,5]cyclohepta[1,2-b]pyridin-5-one having a melting point of 218°–219° C.

IR (KBr) cm$^{-1}$: 1610, 1590, 1505, 1340.

The following compound was obtained in a similar manner.

2-Nitro-6,11-dihydrodibenz[b,e]oxepin-11-one: IR (KBr) cm$^{-1}$: 1660, 1600, 1510, 1350, 1330, 1290, 1270, 990.

REFERENCE EXAMPLE 4

4.46 g of 7-methyl-10,11-dihydro-5H-benzo-[4,5]cyclohepta[1,2-b]pyridin-5-one was dissolved in 22 ml of ethanol. To the solution was added 0.39 g of sodium borohydride with water-cooling. The resulting mixture was stirred for 1 hour at room temperature. To the reaction mixture was added 44 ml of water. The resulting crystals were collected by filtration and dried to obtain 4.19 g of 5-hydroxy-7-methyl-10,11-dihydro-5H-benzo[4,5]cyclohepta[1,2-b]pyridine. They were recrystallized from ethanol to obtain 3.90 g of colorless crystals having a melting point of 202°–203° C.

IR (KBr) cm$^{-1}$: 3120, 1565, 1430, 1040, 810.

NMR (d$_6$-DMSO) δ value: 2.24 (3H,s), 3.20 (4H,bs), 6.02 (2H,bs), 6.86–7.30 (4H,m), 7.90 (1H,dd,J=8 Hz,J=2 Hz), 8.30 (1H,dd,J=5 Hz,J=2 Hz).

REFERENCE EXAMPLE 5

In a manner similar to that in Reference Example 4, there was obtained 5-hydroxy-7-nitro-10,11-dihydro-5H-benzo[4,5]cyclohepta[1,2-b]pyridine having a melting point of 222°–223° C. (ethanol).

IR (KRr) cm$^{-1}$: 3050, 1580, 1520, 1430, 1340, 1040.

NMR (CDCl$_3$-d$_6$-DMSO) δ value: 3.20 (4H,bs), 6.20 (2H,bs), 6.90–7.40 (2H,m), 7.75–8.10 (2H,m), 8.10–8.60 (2H,m).

The compounds shown in Table 4 were obtained in a similar manner.

The mixture was stirred for 2 hours at room temperature. The reaction mixture was washed with water. 250 ml of water was added thereto and the mixture was adjusted to pH 3.0 with concentrated hydrochloric acid. The aqueous layer was separated, washed with methylene chloride, and adjusted to pH 10.0 with a 10% aqueous sodium hydroxide solution. The resulting crystals were collected by filtration and dried to obtain 23.7 g of colorless crystals of 5-(piperazin-1-yl)-10,11-dihydro-5H-benzo[4,5]cyclohepta[1,2-b]pyridine dihydrate having a melting point of 93°-94° C.

IR (KBr) cm$^{-1}$: 3400, 3230, 1440, 1315, 1135, 765.

TABLE 4

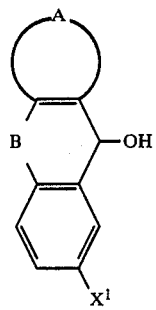

| A | B\ / \\ | X$^1$ | Melting point (°C.) | IR (KBr): cm$^{-1}$ |
|---|---|---|---|---|
| N=CH—CH=CH *1 | (benzene) | —NHAc | 228–229 (EtOH) | 3400, 3230, 1670, 1585, 1535, 1490, 1430, 1400, 1305, 810 |
| N=CH—CH=CH *2 | (benzene) | —OSi+ | 170–171 (IPE) | 3100, 1490, 1280, 860 |
| N=CH—CH=CH | (benzene) | —NO$_2$ | 247–249 (decomposed) (CHCl$_3$—EtOH) | 3050, 2800, 1570, 1520, 1340, 1050, 860, 810 |
| N=CH—CH=CH | (benzene) | —Cl | 245–250 (EtOH—H$_2$O) | 3125, 1250, 1085, 1050, 850, 820 |
| CH=CH—C(NO$_2$)=CH | (thiophene) | —H | 182–183 (AcOEt) | 3420, 1520, 1340, 1180, 1030, 750 |
| CH=CH—C(NO$_2$)=CH | (furan) | —H | 181–183 (EtOH-THF) | 3470, 1600, 1560, 1480, 1300, 1220 |
| CH=CH—C(NO$_2$)=CH | (benzene) | —H | 152–156 (EtOH—H$_2$O) | 3250, 1515, 1335, 1180, 1035, 750 |

*1 As the starting material, there was used 7-acetylamino-10,11-dihydro-5H-benzo[4,5]-cyclohepta[1,2-b]pyridin-5-one having a melting point of 131–133° C. obtained by reacting 7-amino-10,11-dihydro-5H-benzo[4,5]cyclohepta[1,2-b]pyridin-5-one with acetic anhydride.

*2 As the starting material, there was used 7-tert-butyldimethylsilyloxy-10,11-dihydro-5H-benzo[4,5]cyclohepta[1,2-b]pyridin-5-one of oily form obtained by reacting 7-hydroxy-10,11-dihydro-5H-benzo[4,5]cyclohepta[1,2-b]pyridin-5-one with tert-butyldimethylsilyl chloride in the presence of triethylamine.

REFERENCE EXAMPLE 6

(1) 21.1 g of 5-hydroxy-10,11-dihydro-5H-benzo[4,5-]cyclohepta[1,2-b]pyridine was suspended in 100 ml of methylene chloride. To the suspension was added 35.7 g of thionyl chloride with water-cooling. The resulting mixture was stirred for 1 hour at room temperature. The solvent was removed by distillation under reduced pressure to obtain crystals of 5-chloro-10,11-dihydro-5H-benzo[4,5]cyclohepta[1,2-b]pyridine hydrochloride. The crystals were suspended in 100 ml of methylene chloride.

(2) The suspension obtained in the above (1) was added to a solution of 43.1 g of anhydrous piperazine dissolved in 430 ml of methylene chloride, at −20° C.

| NMR (CDCl$_3$) δ value: |
| --- |
| 2.14–2.30 (4H,m), 2.65–3.33 (6H,m), |
| 3.54–4.52 (m) ⎫ |
| 3.90 (s)       ⎬ 3H, |
| 6.82–7.23 (5H,m), |
| 7.41 (1H,dd,J = 7Hz,J = 2Hz), |
| 8.36 (1H,dd,J = 5Hz,J = 2Hz), |

Water content (Karl Fischer's method): 11.19% (calculated: 11.42%)

The following compound was obtained in a similar manner.

3-Nitro-5-(piperazin-1-yl)-10,11-dihydro-5H-dibenzo[a,d]cycloheptene;

Melting point: 227°–229° C. (decomposed) (benzene)

IR (KBr) cm$^{-1}$: 2920, 2780, 1515, 1440, 1340, 1130, 1090, 1000, 830, 800, 775.

REFERENCE EXAMPLE 7

(1) 16.6 g of methyl o-anisate was dissolved in 100 ml of trifluoroacetic acid. Thereto was added 14.0 g of hexamethylenetetramine with ice-cooling. The mixture was refluxed for 2 hours. The solvent was removed by distillation under reduced pressure. The residue was poured into 120 ml of water. The mixture was neutralized with sodium hydrogencarbonate and then extracted with ethyl acetate. The extract was washed with water and a saturated aqueous sodium chloride solution in this order and then dried over anhydrous magnesium sulfate. The solvent was removed by distillation under reduced pressure. The residue was purified by a column chromatography (eluant: n-hexane/ethyl acetate=2/1) to obtain 16.1 g of methyl 5-formyl-2-methoxybenzoate. It was recrystallized from diisopropyl ether to obtain 14.0 g of colorless crystals having a melting point of 85°–86° C.

IR (KBr) cm$^{-1}$: 1700, 1680, 1435, 1265, 1210, 1010, 820.

(2) 13.6 g of methyl 5-formyl-2-methoxybenzoate was dissolved in 68 ml of ethanol. Thereto was added 24 ml of an aqueous solution containing 4.0 g of potassium hydroxide. The mixture was stirred for 1 hour at room temperature. The solvent was removed by distillation under reduced pressure to obtain potassium 5-formyl-2-methoxybenzoate.

(3) The potassium 5-formyl-2-methoxybenzoate obtained in the above (2) was suspended in 68 ml of N,N-dimethylformamide. To the suspension was added 9.1 g of ethyl chlorocarbonate at −15° C. The mixture was stirred for 1 hour at the same temperature. The reaction mixture was added to 68 ml of concentrated ammonia water with ice-cooling. The resulting mixture was stirred for 1 hour at the same temperature. 136 ml of water was added to the reaction mixture. The resulting crystals were collected by filtration and dried to obtain 6.3 g of 5-formyl-2-methoxybenzamide. It was recrystallized from a mixed solvent of chloroform and ethyl acetate to obtain 4.7 g of colorless crystals having a melting point of 150°–153° C.

IR (KBr) cm$^{-1}$: 3400, 1700, 1660, 1580, 1435, 1260, 1205, 1020, 820.

REFERENCE EXAMPLE 8

(1) 3.92 g of 3-dimethoxymethylbenzoic acid and 2.22 g of triethylamine were dissolved in 40 ml of methylene chloride. To the solution was dropwise added 2.28 g of ethyl chlorocarbonate at −30° to −20° C. The mixture was stirred for 30 minutes at the same temperature. The mixture was then cooled to −55° C., and 5.00 g of hydrazine hydrate was added thereto. The temperature of the mixture was elevated to room temperature. The methylene chloride layer was separated, washed with water and a saturated aqueous sodium chloride solution in this order and dried over anhydrous magnesium sulfate. The solvent was removed by distillation under reduced pressure. The residue was purified by a column chromatography (eluant: chloroform/ethanol=30/1) to obtain 4.13 g of colorless oily 3-dimethoxymethylbenzhydrazide.

IR (neat) cm$^{-1}$: 3300, 2925, 1630, 1330, 1100, 1050, 750.

(2) 2.1 g of 3-dimethoxymethylbenzhydrazide and 12.7 g of methyl orthoformate were reacted at atmospheric pressure for 24 hours while distilling off the methanol formed. Excessive methyl orthoformate was removed by distillation under reduced pressure. The residue was purified by a column chromatography (eluant: n-hexane/ethyl acetate=3/1) to obtain 1.35 g of colorless oily 2-(3-dimethoxymethylphenyl)-1,3,4-oxadiazole.

IR (neat) cm$^{-1}$: 2925, 1360, 1200, 1100, 1050, 720.

(3) 1.10 g of 2-(3-dimethoxymethylphenyl)-1,3,4-oxadiazole was dissolved in 8.8 ml of ethyl acetate. To the solution was added 8 ml of water. The mixture was adjusted to pH 1.5 with dilute hydrochloric acid and stirred for 4 hours at room temperature. The reaction mixture was neutralized with sodium hydrogencarbonate. The organic layer was separated, washed with water and a saturated aqueous sodium chloride solution in this order, and dried over anhydrous magnesium sulfate. The solvent was removed by distillation under reduced pressure. The residue was recrystallized from diisopropyl ether to obtain 740 mg of colorless crystals of 2-(3-formylphenyl)-1,3,4-oxadiazole having a melting point of 124°–125° C.

IR (KBr) cm$^{-1}$: 3150, 1690, 1190, 1100, 730.

REFERENCE EXAMPLE 9

5.00 g of 6-bromoindole was added to 25 ml of N,N-dimethylformamide. To the mixture was added 4.37 g of iodomethane in the presence of 1.12 g of sodium hydride (purity: 60%). The resulting mixture was stirred for 1 hour at room temperature to obtain 5.67 g of 6-bromo-1-methylindole. 2.10 g of this compound was dissolved in 21 ml of diethyl ether. Into the solution was dropwise added 7.0 ml of a 1.5M n-hexane solution of n-butyllithium at −45° to −40° C. in a nitrogen atmosphere. The resulting mixture was stirred for 1 hour at room temperature. To the reaction mixture was added 1.46 g of N,N-dimethylformamide at −30° to −20° C. The mixture was stirred for 30 minutes at the same temperature. The temperature of the reaction mixture was elevated to room temperature. 30 ml of water and 10 ml of ethyl acetate were added thereto. The mixture was adjusted to pH 8.0 with dilute hydrochloric acid. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: n-hexane/ethyl acetate=10/1) to obtain 1.09 g of light brown solid 6-formyl-1-methylindole.

IR (KBr) cm$^{-1}$: 1670, 1600, 1300, 1180, 830, 740.

The following compound was obtained in a similar manner.

7-Formyl-1-methylindole
Melting point: 79°–80° C.
IR (KBr) cm 1655, 1290, 1245, 1090, 995, 795, 775, 730.

REFERENCE EXAMPLE 10

8.16 g of 2,5-dimethylbenzothiazole was dissolved in 50 ml of carbon tetrachloride. To the solution were added 8.9 g of N-bromosuccinimide and 82 mg of benzoyl peroxide. The mixture was refluxed for 3 hours. The resulting insolubles were removed by filtration. The solvent of the filtrate was removed by distillation under reduced pressure to obtain 5-bromomethyl-2-methylbenzothiazole. It was suspended in 100 ml of 50% acetic acid. To the suspension was added 14.00 g of hexamethylenetetramine, and the mixture was refluxed for 1 hour. The reaction mixture was mixed with 200 ml of water. The resulting mixture was extracted with ethyl acetate. The extract was washed with a saturated aqueous sodium hydrogencarbonate solution, water and a saturated aqueous sodium chloride solution in this order, and dried over anhydrous magnesium sulfate. The solvent was removed by distillation under reduced pressure. The residue was purified by a column chromatography (eluant: n-hexane/ethyl acetate=3/1) to obtain 3.54 g of colorless crystals of 2-methyl-5-formylbenzothiazole having a melting point of 92°–94° C.

IR (KBr) cm$^{-1}$: 1680, 1595, 1280, 1170.

The compounds shown in Table 5 were obtained in a similar manner.

TABLE 5

HC—R
‖
O

| R | Melting point (°C.) | IR (KBr): cm$^{-1}$ |
|---|---|---|
| (benzothiazole-type, N=N) | 139–142 (AcOEt) | 1670, 1380, 1290, 1050, 860, 800 |
| (benzothiazole with Me, =N) | 100–101 (EtOH) | 1670, 1560, 1520, 1380, 1270, 1230, 1180, 790 |
| (pyridothiadiazole, N–S–N) | 99–101 (IPE) | 1675, 1520, 1410, 1240, 800, 755 |
| (benzimidazole, HN–N=N) | 220–223 (AcOEt) | 3260, 1660, 1605, 1245, 1025, 755 |

REFERENCE EXAMPLE 11

(1) 2.40 g of sodium hydride (purity: 60%) was suspended in 60 ml of tetrahydrofuran. To the suspension was dropwise added 13.5 g of ethyl diethylphosphonoacetate with ice-cooling. The mixture was stirred for 30 minutes at room temperature. To the resulting reaction mixture was dropwise added a solution of 9.06 g of 4-methoxy-3-nitrobenzaldehyde dissolved in 30 ml of tetrahydrofuran, with ice-cooling. The mixture was stirred for 30 minutes at the same temperature. To the reaction mixture was added 100 ml of ethyl acetate and 50 ml of water, and the organic layer was separated. The organic layer was washed with water and a saturated aqueous sodium chloride solution in this order, and dried over anhydrous magnesium sulfate. The solvent was removed by distillation under reduced pressure to obtain ethyl (E)-3-(4-methoxy-3-nitrophenyl)acrylate.

(2) The ethyl (E)-3-(4-methoxy-3-nitrophenyl)-acrylate obtained in the above (1) was dissolved in 150 ml of tetrahydrofuran. To the solution was dropwise added 91.5 ml of a 1M toluene solution of diisobutyl-aluminum hydride, at −70° to −65° C. in a nitrogen atmosphere. The mixture was stirred for 1 hour at the same temperature. To the reaction mixture were added 100 ml of water and 100 ml of ethyl acetate. The resulting insolubles were removed by filtration. An organic layer was separated from the filtrate, washed with water and a saturated aqueous sodium chloride solution in this order, and dried over anhydrous magnesium sulfate. The solvent was removed by distillation under reduced pressure to obtain 9.01 g of (E)-3-(4-methoxy-3-nitrophenyl)allyl alcohol. It was recrystallized from benzene to obtain 8.02 g of colorless crystals having a melting point of 78°–79° C.

IR (KBr) cm$^{-1}$: 3300, 1610, 1520, 1350, 1265, 1000, 960.

NMR (CDCl$_3$) δ value: 1.62 (1H,bs), 3.95 (3H,s), 4.31 (2H,d,J=4 Hz), 6.25 (1H,dt,J=16 Hz,J=4 Hz), 6.62 (1H,d,J=16 Hz), 7.02 (1H,d,J=9 Hz), 7.53 (1H,dd,J=9 Hz,J=2 Hz), 7.83 (1H,d,J=2 Hz)

REFERENCE EXAMPLE 12

9.86 g of ethyl diethylphosphonoacetate and 4.86 g of triethylamine were added to a solution of 3.89 g of lithium bromide dissolved in 80 ml of tetrahydrofuran, in a nitrogen atmosphere. The mixture was stirred for 10 minutes at room temperature. To the reaction mixture was added 6.09 g of 4-methylthiobenzaldehyde, and the mixture was stirred for 5 hours at the same temperature. The resulting precipitate was removed by filtration. The filtrate was mixed with 60 ml of ethyl acetate. The mixture was washed with water and a saturated aqueous sodium chloride solution in this order, and dried over anhydrous magnesium sulfate. The solvent was removed by distillation under reduced pressure to obtain 7.67 g of ethyl (E)-3-(4-methylthiophenyl)acrylate. It was recrystallized from ethanol to obtain 7.17 g of colorless crystals having a melting point of 45°–46° C.

IR (KBr) cm$^{-1}$: 1700, 1620, 1580, 1485, 1305, 1205, 1170, 1090, 1030, 1000, 805.

The compounds shown in Table 6 were obtained in a similar manner.

TABLE 6

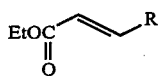

| R | Melting point (°C.) | IR (KBr): cm$^{-1}$ |
|---|---|---|
| 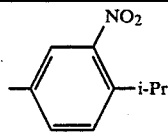 | 56–57 | 3060, 2960, 1710, 1640, 1530, 1365, 1315, 1215, 1190, 985, 835 |
| 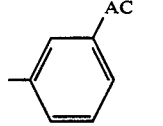 | 64–65 | 1700, 1670, 1350, 1310, 1250, 1180, 1030 |
| 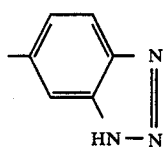 | 137–141 (IPE) | 3200, 1670, 1630, 1320, 1280, 1200 |
| 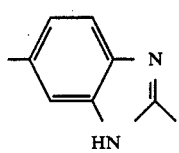 | 135–137 (IPE) | 1720, 1620, 1260, 1220, 1030, 800 |
| 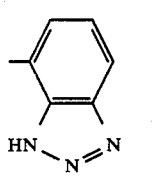 | 160–162 (IPE) | 3150, 1710, 1630, 1240, 1160, 1095, 800 |

REFERENCE EXAMPLE 13

(1) 13.2 g of ethyl (E)-3-(4-isopropyl-3-nitrophenyl)acrylate was dissolved in 330 ml of 80% ethanol. Thereto were added 27.9 g of an iron powder and 4.17 ml of concentrated hydrochloric acid at room temperature. The mixture was refluxed for 1.5 hours. The reaction mixture was neutralized with sodium hydrogencarbonate. The resulting insolubles were removed by filtration and the filtrate was subjected to distillation under reduced pressure to remove the solvent. To the residue were added 100 ml of water and 200 ml of diethyl ether. The mixture was adjusted to pH 1.0 with concentrated hydrochloric acid. The resulting crystals were filtered. The crystals obtained and the separated aqueous layer obtained from the filtrate were combined and neutralized with sodium hydrogencarbonate. Then, the mixture was extracted with ethyl acetate. The extract was washed with water and a saturated aqueous sodium chloride solution in this order and dried over anhydrous magnesium sulfate. The solvent was removed by distillation under reduced pressure to obtain 10.0 g of brown oily ethyl (E)-3-(3-amino-4-isopropylphenyl)acrylate.

IR (neat) cm$^{-1}$: 3400, 2960, 1710, 1630, 1180.

(2) 4.67 g of ethyl (E)-3-(3-amino-4-isopropylphenyl)acrylate was dissolved in 46.7 ml of acetic acid. To the solution was added 46.7 ml of 2N hydrochloric acid with ice-cooling. To the mixture was dropwise added 10 ml of an aqueous solution containing 1.52 g of sodium nitrite. The mixture was stirred for 30 minutes at the same temperature. The reaction mixture was added to 30 ml of 6N hydrochloric acid solution containing 2.18 g of cuprous chloride, with ice-cooling. The mixture was stirred for 1 hour at the same temperature and then for 2 hours at room temperature. To the reaction mixture was added 100 ml of ethyl acetate. The organic layer was separated and washed with water. Thereto was added 50 ml of water. The mixture was adjusted to about pH 7 with sodium hydrogencarbonate. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: n-hexane/ethyl acetate=20/1) to obtain 3.57 g of colorless oily ethyl (E)-3-(3-chloro-4-isopropylphenyl)acrylate.

IR (neat) cm$^{-1}$: 1715, 1635, 1310, 1175.

REFERENCE EXAMPLE 14

(1) 10.9 g of ethyl (E)-3-(3-acetylphenyl)acrylate was dissolved in 50 ml of ethanol and 5 ml of dioxane. To the solution was dropwise added 8.8 g of bromine in 2 hours at 15° to 20° C. The mixture was stirred for 1 hour at the same temperature. The solvent was removed by distillation under reduced pressure to obtain ethyl (E)-3-[3-(2-bromoacetyl)phenyl]acrylate.

(2) The ethyl (E)-3-[3-(2-bromoacetyl)phenyl]-acrylate obtained in the above (1) was dissolved in 50 ml of formamide. The solution was refluxed for 1 hour. The reaction mixture was mixed with 100 ml of water. The mixture was extracted with chloroform. The extract was washed with water and dried over anhydrous magnesium sulfate. The solvent was removed by distillation under reduced pressure. The residue was purified by a column chromatography (eluant: chloroform/ethanol=20/1) to obtain 6.05 g of light yellow oily ethyl (E)-3-[3-(4-imidazolyl)phenyl]-acrylate.

IR (neat) cm$^{-1}$: 2970, 1700, 1635, 1305, 1190.

REFERENCE EXAMPLE 15

(1) 1.91 g of ethyl (E)-3-(3-aminophenyl)acrylate and 1.11 g of triethylamine were dissolved in 28 ml of methylene chloride. To the solution was added 1.48 g of 4-chlorobutyryl chloride at −60° C. The mixture was stirred for 30 minutes at room temperature. To the reaction mixture was added 20 ml of water. The organic layer was separated, washed with 20 ml of a saturated aqueous sodium chloride solution, and dried over anhydrous magnesium sulfate. The solvent was removed by distillation under reduced pressure. The residue was recrystallized from diisopropyl ether to obtain 2.64 g of colorless crystals of ethyl (E)-3-[3-(4-chlorobutyrylamino)phenyl]acrylate having a melting point of 99°–100° C.

IR (KBr) cm$^{-1}$: 3350, 1680, 1475, 1270, 1220, 800.

(2) 1.48 g of ethyl (E)-3-[3-(4-chlorobutyrylamino)phenyl]acrylate was dissolved in 15 ml of N,N-dimethylformamide. To the solution was added 0.23 g of sodium hydride (purity: 60%) with ice-cooling. The mixture was stirred for 2 hours at room temperature. The reaction mixture was mixed with 50 ml of ice water and 50 ml of ethyl acetate. The organic layer was separated, washed with water and a saturated aqueous sodium chloride solution in this order, and dried over anhydrous magnesium sulfate. The solvent was removed by distillation under reduced pressure. The residue was recrystallized from a mixed solvent of isopropyl alcohol and diisopropyl ether to obtain 1.04 g of colorless crystals of ethyl (E)-3-[3-(2-oxo-1-pyrrolidinyl)phenyl]acrylate having a melting point of 88°–89° C.

IR (KBr) cm$^{-1}$: 1680, 1635, 1450, 1300, 1190, 790.

REFERENCE EXAMPLE 16

1.73 g of (E)-3-(3-cyanophenyl)acrylic acid was suspended in 8.7 ml of tetrahydrofuran. To the suspension was added 1.11 g of triethylamine. To the mixture was dropwise added a solution of 1.14 g of ethyl chlorocarbonate dissolved in 3.0 ml of tetrahydrofuran, at −20° to −10° C. The mixture was stirred for 30 minutes at 0° C. The reaction mixture was mixed with 2 ml of ethyl acetate and 20 ml of a saturated aqueous sodium chloride solution. The organic layer was separated and washed with a saturated aqueous sodium chloride solution to obtain a solution containing a mixed acid anhydride of (E)-3-(3-cyanophenyl)acrylic acid. To this solution was added 380 mg of sodium borohydride with ice-cooling. The mixture was stirred for 1 hour at the same temperature. To the reaction mixture was added 20 ml of water and 10 ml of ethyl acetate. The organic layer was separated, washed with a saturated aqueous sodium chloride solution, and dried over anhydrous magnesium sulfate. The solvent was removed by distillation under reduced pressure. The residue was purified by a column chromatography (eluant: n-hexane/acetone=5/1) to obtain 1.37 g of colorless oily (E)-3-(3-cyanophenyl)allyl alcohol.

IR (neat) cm$^{-1}$: 3375, 2225, 1080, 1015, 965.

NMR (CDCl$_3$) δvalue: 2.19 (1H,bs), 4.35 (2H,d,J=4 Hz), 6.35 (1H,dt,J=16 Hz,J=4 Hz), 6.68(1H,d,J=16 Hz), 7.20–7.72 (4H,m).

REFERENCE EXAMPLE 17

(1) 10.9 g of ethyl (E)-3-(3-acetylphenyl)acrylate was dissolved in 100 ml of benzene. To the solution were added 4.66 g of ethylene glycol and 480 mg of p-toluenesulfonic acid monohydrate. The mixture was subjected to azeotropic removal of water formed for 4 hours. The reaction mixture was washed with a saturated aqueous sodium hydrogencarbonate solution, water and a saturated aqueous sodium chloride solution in this order, and dried over anhydrous magnesium sulfate. The solvent was removed by distillation under reduced pressure to obtain 10.5 g of colorless oily ethyl (E)-3-[3-(1,1-ethylenedioxy)ethylphenyl]acrylate.

IR (neat) cm$^{-1}$: 2970, 1710, 1630, 1310, 1180.

(2) 5.25 g of ethyl (E)-3-[3-(1,1-ethylenedioxy)-ethylphenyl]acrylate was reacted in the same manner as in Reference Example 11-(2) to obtain 3.17 g of colorless oily (E)-3-(3-acetylphenyl)allyl alcohol.

IR (neat) cm$^{-1}$: 3400, 2850, 1670, 1590, 1420, 1360, 1280.

REFERENCE EXAMPLE 18

(1) 6.67 g of ethyl (E)-3-(4-hydroxy-3-methoxyphenyl)acrylate and 5.69 g of 3-bromopyridine were dissolved in 13.3 ml of hexamethyl phosphoric triamide. To the solution were added 4.15 g of potassium carbonate and 0.57 g of a copper powder. The mixture was stirred for 3 hours at 160° C. in a nitrogen atmosphere. The reaction mixture was mixed with 100 ml of ice water and 100 ml of ethyl acetate. The resulting insolubles were removed by filtration. An organic layer was separated, washed with water and a saturated aqueous sodium chloride solution in this order, and dried over anhydrous magnesium sulfate. The solvent was removed by distillation under reduced pressure. The residue was purified by a column chromatography (eluant: benzene/ethyl acetate=10/1) to obtain 1.93 g of light yellow oily ethyl (E)-3-[3-methoxy-4-(3-pyridyloxy)phenyl]acrylate.

IR (neat) cm$^{-1}$: 2960, 1700, 1500, 1470, 1420, 1270, 1180, 1160, 1030, 860, 700.

(2) 2.99 g of ethyl (E)-3-[3-methoxy-4-(3-pyridyloxy)phenyl]acrylate was dissolved in 30 ml of anhydrous toluene. To the solution was dropwise added 22.0 ml of a 1M toluene solution of diisobutylaluminum hydride at −50° C. in a nitrogen atmosphere. The mixture was stirred for 30 minutes at the same temperature. To the reaction mixture was dropwise added 1.6 ml of water. The mixture was stirred for 1 hour at room temperature. The resulting insolubles were removed by filtration. The filtrate was dried over anhydrous magnesium sulfate. The solvent was removed by distillation under reduced pressure to obtain 2.57 g of colorless oily (E)-3-[3-methoxy-4-(3-pyridyloxy)phenyl]allyl alcohol.

IR (neat) cm$^{-1}$: 3300, 1500, 1470, 1420, 1270, 1230, 1030.

NMR (CDCl$_3$) δvalue: 2.87 (1H,s), 3.79 (3H,s), 4.32 (2H,d,J=4 Hz), 6.27 (1H,dt,J=16 Hz,J=4 Hz), 6.65 (1H,d,J=16 Hz), 6.80–7.30 (5H,m), 8.10–8.40 (2H, m).

REFERENCE EXAMPLE 19

Reaction was effected in the same manner as in Reference Example 11, 12, 16 or 18 to obtain compounds shown in Tables 7, 8 and 9.

TABLE 7

[Structure: benzene ring with R³ (position 2), R⁴ (position 3), R⁵ (position 4), and -CH=CH-CH₂OH substituent]

| R³ | R⁴ | R⁵ | Melting point (°C.) | IR: cm⁻¹ | NMR (CDCl₃) δ value: |
|---|---|---|---|---|---|
| —OMe | —OMe | —OMe | Oily | (Neat) 3380, 2925, 1590, 1485, 1455, 1410, 1290, 1090, 970, 795 | 1.73 (1H, bs), 3.86 (9H, s), 4.30 (2H, d, J = 5Hz), 6.25 (1H, dt, J = 16Hz, J = 5Hz), 6.64 (d, J = 9Hz) ⎱ 2H, 6.83 (d, J = 16Hz) ⎰ 7.15 (1H, d, J = 9Hz) |
| —H | —O—C₆H₅ (phenoxy) | —OMe | Oily | (Neat) 3350, 1510, 1490, 1270, 1220, 1130, 1020, 970, 750 | 1.93 (1H, bs), 3.78 (3H, s), 4.19 (2H, d, J = 5Hz), 6.07 (1H, dt, J = 16Hz, J = 5Hz), 6.49 (1H, d, J = 16 Hz), 6.70–7.60 (8H, m) |
| —H | —CONH₂ | —OMe | 139~142*¹ | (KBr) 3300, 1645, 1610, 1590, 1430, 1250, 970 | (CDCl₃-CD₃OD) 2.84 (3H, bs), 3.98 (3H, s), 4.27 (2H, d, J = 5Hz), 6.27 (1H, dt, J = 16Hz, J = 5Hz), 6.64 (1H, d, J = 16Hz), 6.96 (1H, d, J = 9Hz), 7.51 (1H, dd, J = 9Hz, J = 2Hz), 8.18 (1H, d, J = 2Hz) |
| —H | —F | —F | Oily | (Neat) 3320, 1595, 1505, 1290, 1270, 965 | 1.53 (1H, s), 4.31 (2H, d, J = 5Hz), 6.22 (1H, dt, J = 16Hz, J = 5Hz), 6.60 (1H, d, J = 16 Hz), 6.80–7.48 (3H, m) |
| —H | —H | —C₆H₅ (phenyl) | 154~158*² | (KBr) 3280, 1480, 1400, 1080, 1000, 970, 760 | (d₆-DMSO) 4.17 (2H, d, J = 4Hz), 4.70 (1H, bs), 6.37 (1H, dt, J = 16Hz, J = 4Hz), 6.68 (1H, d, J = 16Hz), 7.25–7.73 (9H, m) |

*¹Recrystallized from chloroform-methanol.
*²Recrystallized from ethyl acetate.

TABLE 8

[Structure: benzene ring with R⁴ (position 3), R⁵ (position 4), and -CH=CH-CH₂OH substituent]

| R⁴ | R⁵ | Melting point (°C.) | IR: cm⁻¹ | NMR(CDCl₃) δ value: |
|---|---|---|---|---|
| —O-(3-pyridyl) | —OMe | Oily | (Neat) 3300, 1500, 1420, 1270, 1230, 1120, 1020 | 2.76 (1H, s), 3.78 (3H, s), 4.26 (2H, d, J=4Hz), 6.14 (1H, dt, J=16Hz, J=4Hz), 6.56 (1H, d, J=16Hz), 6.70–7.40 (5H, m), 8.08–8.44 (2H, m) |
| —H | —SMe | 92~93*³ | (KBr) 3250, 1585, 1485, 1395, 1080, 1015, 995, 960, 840, 785 | 1.76 (1H, s), 2.46 (3H, s), 4.28 (2H, d, J=5Hz), 6.24 (1H, dt, J=16Hz, J=5Hz), 6.60 (1H, d, J=16Hz), 7.04–7.44 (4H, m) |
| ¹—H | —SOMe | — | (KBr) 3320, 1400, 1085, 1025, 1010, 965, 850 | 2.71 (3H, s), 2.93 (1H, bs), 4.32 (2H, d, J=4Hz), 6.36 (1H, dt, J=16Hz, J=4Hz), 6.69 (1H, d, J=16Hz), 7.32–7.68 (4H, m) |
| ²—H | —SO₂Me | 123~125*² | (KBr) 3510, 3330, | 1.97 (1H, bs), 3.04 (3H, s), 4.36 (2H, d, J=4Hz), |

TABLE 8-continued

[Structure: R4, R5 substituted phenyl-CH=CH-CH2OH]

| R⁴ | R⁵ | Melting point (°C.) | IR: cm⁻¹ | NMR(CDCl₃) δ value: |
|---|---|---|---|---|
| | | | 1285, 1145, 1080, 965, 765 | 6.42(1H, dt, J=16Hz, J=4Hz), 6.75(1H, d, J=16Hz) 7.49(2H, d, J=8Hz), 7.87(2H, d, J=8Hz) |
| ³—H | —CH₂OSi⟨ (t-Bu)(Me)₂ | — | (KBr) 3350, 2925, 2850, 1460, 1250, 1080, 970, 840, 780 | 0.09(6H, s), 0.94(9H, s), 2.34(1H, s), 4.23(2H, d, J=4Hz), 4.70(2H, s), 6.23(1H, dt, J=16Hz, J=4Hz), 6.60(1H, d, J=16Hz), 7.28(4H, bs) |
| ⁴—H | —OSi⟨ (t-Bu)(Me)₂ | Oily | (Neat) 3300, 2930, 2850, 1600, 1505, 1260, 970, 915, 840, 800, 785 | 0.19(6H, s), 0.98(9H, s), 1.57(1H, bs), 4.27(2H, d, J=5Hz), 6.17(1H, dt, J=16Hz, J=5Hz), 6.58(1H, d, J=16Hz), 6.77(2H, d, J=9Hz), 7.25(2H, d, J=9Hz) |

*²Recrystallized from ethyl acetate.
*³Recrystallized from benzene.
¹As the starting material, there was used ethyl (E)-3-(4-methylsulfinylphenyl)-acrylate [IR (KBr) cm⁻¹: 1710, 1635, 1310, 1270, 1175, 1085, 1045, 825] obtained by reacting ethyl (E)-3-(4-methylthiophenyl)acrylate with one equivalent of m-chloroperbenzoic acid.
²As the starting material, there was used ethyl (E)-3-(4-methylsulfonylphenyl)-acrylate having a melting point of 92–94° C. obtained by reafting ethyl (E)-3-(4-methylthiophenyl)acrylate with two equivalents of m-chloroperbenzoic acid.
³, ⁴As the starting material, there was used a silyl compound obtained by reacting a corresponding hydroxyl compound with tert-butyldimethylsilyl chloride in the presence of triethylamine.

TABLE 9

[Structure: HO-CH2-CH=CH-R]

| R | Melting point (°C.) | IR: cm⁻¹ |
|---|---|---|
| 3-F-phenyl | Oily | (Neat) 3350, 2850, 1570, 1440, 1260, 1140, 970, 780 |
| 4-(allyloxy)-3-NO₂-phenyl | Oily | (Neat) 3350, 1615, 1520, 1350, 1270, 990, 965 |
| 4-OEt-3-NO₂-phenyl | 58–59 (AcOEt-n-hexane) | (KBr) 3250, 1620, 1525, 1340, 1260, 960 |
| 3-(O-i-Pr)-phenyl | Oily | (Neat) 3350, 2960, 1600, 1250, 1110, 970, 780 |
| 2-(O-i-Pr)-5-NO₂-phenyl | Oily | (Neat) 3375, 1525, 1350, 1270, 1105 |
| 4-Cl-3-NO₂-phenyl | 95–96 (IPE) | (KBr) 3200, 1520, 1360, 1090, 960, 840 |
| 3-(O-t-Bu)-phenyl | Oily | (Neat) 3400, 2970, 1590, 1480, 1360, 1150, 970 |
| 3-NMe₂-phenyl | Oily | (Neat) 3310, 2840, 1590, 1490, 1350, 995, 965, 770 |

TABLE 9-continued
HO⁀⁀⁀R
| R | Melting point (°C.) | IR: cm⁻¹ |
|---|---|---|
| 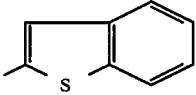 | — | (KBr) 3300, 1430, 950, 750, 730 |
| 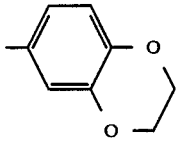 | Oily | (Neat) 3350, 1575, 1495, 1305, 1285, 1255, 1065, 965, 885 |
| 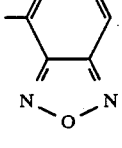 | 63-65 | (KBr) 3250, 1000, 970, 880, 750 |
| 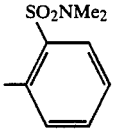 | Oily | (Neat) 3440, 1460, 1330, 1160, 960, 755 |
|  | Oily | (Neat) 3325, 1420, 1125, 970, 740 |
|  | 61-62 (IPE) | (KBr) 3330, 1465, 1445, 1280, 1255, 1075 970, 760, 715 |
| 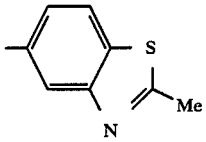 | Oily | (Neat) 3330, 1445, 1250, 1065, 970, 935, 760, 725 |
| 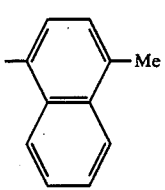 | Oily | (Neat) 3350, 2850, 1420, 1180, 1090, 1010, 970, 790 |
| 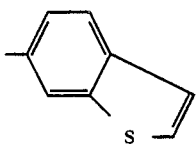 | Oily | (Neat) 3300, 1590, 1370, 1090, 970, 810 |
| 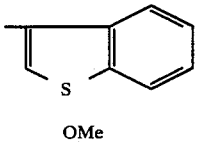 | 99-100 (AcOEt) | (KBr) 3375, 970, 690 |
| 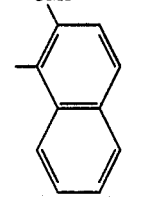 | Oily | (Neat) 3350, 2850, 1420, 970, 760, 740 |
| 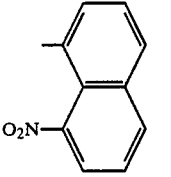 | Oily | (Neat) 3400, 2920, 2830, 1580, 1450, 1250, 1080, 810 |
| 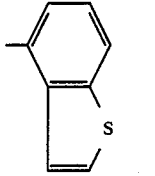 | Oily | (Neat) 3350, 1510, 1350, 1090, 970, 820 |
| 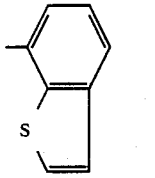 | Oily | (Neat) 3350, 2850, 1450, 1410, 1090, 970, 760 |
| 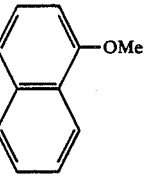 | Oily | (Neat) 3325, 1380, 1080, 965, 785, 735, 695 |
| 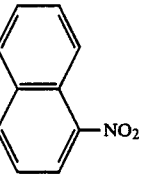 | 72-74 (AcOEt-n-hexane) | (KBr) 3290, 1580, 1260, 1090, 960, 770 |
|  | 106-108 (Benzene) | (KBr) 3520, 1500, 1320, 1110, 790 |

TABLE 9-continued

HO⌒⌒R

| R | Melting point (°C.) | IR: cm⁻¹ |
|---|---|---|
| (4-methylphenyl benzofuran-2-yl) | 64–66 (IPE) | (KBr) 3250, 2820, 1460, 1120, 1080, 1030, 1010, 970, 770 |
| (4-methylphenyl benzothiophene-2-yl) | 97–98 (IPE) | (KBr) 3300, 1410, 1330, 1085, 970 |
| 2,3-dichlorophenyl | 57–58 (n-Hexane) | (KBr) 3200, 1440, 1400, 1180, 1080, 960, 760 |
| benzothiadiazole | 63–65 | (KBr) 3430, 1380, 1270, 1100, 960, 770 |
| 3-NO₂-2-OMe-phenyl | 84–86 | (KBr) 3225, 1520, 1370, 1090 |
| quinolinyl | Oily | (Neat) 3300, 1590, 1490, 1090, 970, 800 |
| 3-NO₂-4-OMe-phenyl | 89–91 (AcOEt—IPE) | (KBr) 3200, 2820, 1570, 1490, 1350, 1250, 1070 |
| 2-methyl-benzothiazole | 108–109 (AcOEt—IPE) | (KBr) 3250, 1330, 1180, 1110, 960, 810, 760 |

TABLE 9-continued

HO⌒⌒R

| R | Melting point (°C.) | IR: cm⁻¹ |
|---|---|---|
| benzothiadiazole | 72–73 (IPE) | (KBr) 3300, 1525, 1080, 905, 755 |
| 3-OSiMe₃-phenyl | Oily | (Neat) 3300, 2925, 2850, 1590, 1480, 1280, 850, 780 |
| 2,4-(N-Tri)(N-Me)-phenyl | — | (KBr) 3200, 1450, 1340, 1290, 1090, 970, 750, 700 |
| 6-NHTri-phenyl | Oily | (Neat) 3400, 3050, 1600, 1480, 1320, 970 |
| 7-CHO-phenyl | 67–60 (Diethyl ether) | (KBr) 3180, 1685, 1005, 975, 790 |
| 8-(N-pyrrolyl)-phenyl | Oily | (Neat) 3350, 2850, 1600, 1580, 1500, 1340, 1070, 970, 730 |
| (2-oxopyrrolidin-1-yl)phenyl | 114–115 (IPE) | (KBr) 3350, 1660, 1600, 1460, 1300, 1110, 970, 770 |
| 5-(N-Tri-oxazoline)-phenyl | 164–166 (AcOEt) | (KBr) 3250, 1600, 1480, 1440, 1150, 960, 750, 700 |

TABLE 9-continued

HO⁓⁓R (structure: HO-CH=CH-R)

| R | Melting point (°C.) | IR: cm$^{-1}$ |
|---|---|---|
| phenyl-substituted phenyl (biphenyl) | 50–51 (IPE) | (KBr) 3350, 1470, 1010, 970, 755, 695 |
| Cl, i-Pr substituted phenyl | Oily | (Neat) 3310, 2950, 965 |
| NO$_2$, i-Pr substituted phenyl | Oily | (Neat) 3325, 2960, 1520, 1355, 970 |
| COOMe substituted phenyl | Oily | (Neat) 3400, 1720, 1430, 1290, 1200, 1100, 960, 750 |
| N-Tri piperazinyl-phenyl [8] | 222–223 (EtOH) | (KBr) 3230, 1485, 1440, 1240, 1020, 970, 745, 695 |
| oxadiazolyl-phenyl | — | (KBr) 3300, 1550, 1080, 960, 730 |

[1] As the starting material, there was used oily 4-allyloxy-3-nitrobenzaldehyde obtained by reacting 4-hydroxy-3-nitrobenzaldehyde with allyl bromide in the presence of potassium carbonate.
[2] As the starting material, there was used oily 4-isopropyloxy-3-nitrobenzaldehyde obtained by reacting 4-hydroxy-3-nitrobenzaldehyde with isopropyl bromide in the presence of triethylamine.
[3] As the starting material, there was used a silyl compound obtained by reacting a corresponding hydroxyl compound with tert-butyldimethylsilyl chloride in the presence of triethylamine.
[4, 5, 9] Since it is uncertain which nitrogen atom in a ring is bound to a triphenylmethyl group, the expression described in the Table was adopted.
[4, 5, 6, 9] As the raw material, there was used a trityl compound obtained by reacting an imino group or an amino group with trityl chloride in the presence of triethylamine.
[7] Ethyl (E)-3-(3-cyanophenyl)acrylate was used as the raw material.
[8] As the raw material, there was used ethyl (E)-3-[3-(1-pyrrolyl)phenyl]acrylate having a melting point of 61°–62° C. obtained by reacting ethyl (E)-3-(3-aminophenyl)acrylate with 2,5-dimethoxytetrahydrofuran.

REFERENCE EXAMPLE 20

3.28 g of methyl 3-formylbenzoate, 4.16 g of malonic acid and 260 mg of piperidine were dissolved in 7.9 ml of pyridine. The solution was stirred for 2 hours at 80° to 85° C. and then for 2.5 hours at 110° to 115° C. To the reaction mixture was added 50 ml of ice water. The mixture was adjusted to pH 2.0 with dilute hydrochloric acid. The resulting crystals were collected by filtration and dried to obtain 3.70 g of colorless crystals of (E)-3-(3-methoxycarbonylphenyl)acrylic acid having a melting point of 180°–183° C.

IR (KBr) cm$^{-1}$: 1725, 1420, 1290, 1240, 760.

The following compounds were obtained in a similar manner.

(E)-3-(1-methyl-6-indolyl)acrylic acid:
Melting point: 173°–178° C. (acetonitrile)
IR (KBr) cm$^{-1}$: 2800, 2500, 1670, 1600, 1310, 980, 800, 710.

(E)-3-[3-(1,3,4-oxadiazol-2-yl)phenyl]acrylic acid:
Melting point: 220° C. (decomposed) (IPE)
IR (KBr) cm$^{-1}$: 2925, 1710, 1640, 1300, 1210, 970.

(E)-3-(1-methyl-7-indolyl)acrylic acid:
Melting point: 219°–220° C. (decomposed) (acetonitrile-water)
IR (KBr) cm$^{-1}$: 1660, 1605, 1525, 795, 735.

REFERENCE EXAMPLE 21

2.59 g of ethyl (E)-3-[3-(2-oxo-1-pyrrolidinyl)phenyl]acrylate was dissolved in 30 ml of ethanol. To the solution was added 520 mg of sodium hydroxide. The mixture was refluxed for 1 hour. The solvent was removed by distillation under reduced pressure. To the residue was added 20 ml of water and 20 ml of diethyl ether. The aqueous layer was separated and adjusted to pH 2.0 with dilute hydrochloric acid. The resulting crystals were collected by filtration and dried to obtain 1.62 g of colorless crystals of (E)-3-[3-(2-oxo-1-pyrrolidinyl)phenyl]acrylic acid having a melting point of 177°–178° C.

IR (KBr) cm$^{-1}$: 2900, 2580, 1680, 1620, 1380, 1290, 980, 785.

The following compounds were obtained in a similar manner.

(E)-3-(benzotriazol-5-yl)acrylic acid
Melting point: Above 240° C.
IR (KBr) cm$^{-1}$: 2800, 1660, 1600, 1310, 1290, 1000, 970, 810.

(E)-3-(benzotriazol-4-yl acrylic acid
Melting point: 267°–270° C. (water)
IR (KBr) cm$^{-1}$: 3400, 3000, 1680, 1285, 1270, 760.

REFERENCE EXAMPLE 22

(E)-3-(imidazol-4-yl)acrylic acid was reacted with chlorotriphenylmethane in N,N-dimethylformamide to obtain (E)-3-(N-triphenylmethylimidazol-4-yl)acrylic acid.

Melting point: 219°–220° C. (decomposed) (ethanol)
IR (KBr) cm$^{-1}$: 3480, 1680, 1635, 1300, 1270, 1180, 745, 690.

REFERENCE EXAMPLE 23

(E)-3-(3-carbamoylphenyl)allyl alcohol was obtained from (E)-3-(3-methoxycarbonylphenyl)allyl alcohol in a manner similar to that in Reference Example 7-(2) and (3).

IR (KBr) cm$^{-1}$: 3340, 3150, 1660, 1625, 1400, 970.

EXAMPLE 1

(1) 2.11 g of 5-hydroxy-10,11-dihydro-5H-benzo[4,5-]cyclohepta[1,2-b]pyridine was suspended in 10 ml of methylene chloride. To the suspension was added 3.57 g of thionyl chloride with water-cooling. The mixture was stirred for 1 hour at room temperature. The solvent was removed by distillation under reduced pressure to obtain crystals of 5-chloro-10,11-dihydro-5H-benzo[4,5-

]cyclohepta[1,2-b]pyridine hydrochloride. The crystals were suspended in 10 ml of methylene chloride.

(2) The suspension obtained in the above (1) was added to a mixture of 2.02 g of 1-[(E)-3-phenylallyl]-piperazine and 2.22 g of triethylamine with ice-cooling. The mixture was stirred for 30 minutes at the same temperature and then for 1 hour at room temperature. After the reaction mixture was washed with water and 25 ml of water was added thereto. The mixture was adjusted to pH 1.0 with dilute hydrochloric acid. The aqueous layer was separated and washed with methylene chloride. Ethyl acetate was added thereto. The mixture was adjusted to pH 7.0 with sodium hydrogencarbonate. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: benzene/ethyl acetate=19/1) to obtain 1.98 g of 5-[4-{(E)-3-phenylallyl}-piperazin-1-yl]-10,11-dihydro-5H-benzo[4,5]cyclohepta[1,2-b]pyridine. It was recrystallized from 70% ethanol to obtain 1.68 g of colorless crystals having a melting point of 130°-131° C.

IR (KBr) cm$^{-1}$: 2930, 2780, 1440, 1133, 995, 965, 745.

| NMR (CDCl$_3$) δ value: |
|---|
| 2.36 (8H,bs), |
| 2.64-3.35 (m) ⎫ |
| 3.07 (d,J = 5Hz) ⎭ 4H, |
| 3.65-4.53 (m) ⎫ |
| 3.92 (s) ⎭ 3H, |
| 6.14 (1H,dt,J = 16Hz,J = 5Hz), |
| 6.51 (1H,d,J = 16Hz), 6.80-7.48 (11H,m), |
| 8.38 (1H,dd,J = 5Hz,J = 2Hz) |

(3) 1.58 g of the 5-[4-{(E)-3-phenylallyl}-piperazin-1-yl]-10,11-dihydro-5H-benzo[4,5]cyclohepta-[1,2-b]pyridine was dissolved in 24 ml of isopropyl alcohol. To the solution was dropwise added 8 ml of a 2N dioxane solution of hydrogen chloride at room temperature. After the completion of the addition, the resulting mixture was stirred for 1 hour at the same temperature. The resulting crystals were collected by filtration to obtain 1.90 g of 5-[4-{(E)-3-phenylallyl}piperazin-1-yl]-10,11-dihydro-5H-benzo-[4,5]cyclohepta[1,2-b]pyridine trihydrochloride having a melting point of 174°-176° C.

IR (KBr) cm$^{-1}$: 2370, 1610, 1440, 1110, 770, 750.

EXAMPLE 2

3.67 g of triphenylphosphine was added to a solution of 1.94 g of (E)-3-(3,4-dimethoxyphenyl)allyl alcohol and 3.98 g of carbon tetrabromide dissolved in 20 ml of benzene, with ice-cooling in a nitrogen atmosphere. The mixture was stirred for 1 hour at the same temperature to obtain a benzene solution of (E)-3-(3,4-dimethoxyphenyl)allyl bromide. To this solution were added 1.11 g of triethylamine and a solution of 3.15 g of 5-(piperazin-1-yl)-10,11-dihydro-5H-benzo[4,5]cyclohepta[1,2-b]pyridine dihydrate dissolved in 12 ml of benzene, with ice-cooling. The mixture was stirred for 2 hours at room temperature. To the reaction mixture was added 30 ml of water. The resulting insolubles were removed by filtration. An organic layer was separated and to the layer was added 30 ml of water. The mixture was adjusted to pH 1.0 with dilute hydrochloric acid. The aqueous layer was separated and 30 ml of ethyl acetate was added thereto. The mixture was adjusted to pH 8.0 with a 10% aqueous sodium hydroxide solution. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: n-hexane/acetone=2/1) to obtain 2.52 g of 5-[4-{(E)-3-(3,4-dimethoxyphenyl)allyl}piperazin-1-yl]-10,11-dihydo-5H-benzo[4,5]cyclohepta[1,2-b]pyridine. It was recrystallized from a mixed solvent of ethyl acetate and n-hexane to obtain 2.13 g of colorless crystals having a melting point of 135°-136° C.

IR (KBr) cm$^{-1}$: 2910, 2785, 1440, 1265, 1135, 1020, 995, 965, 765.

| NMR (CDCl$_3$) δ value: |
|---|
| 2.38 (8H,bs), |
| 2.62-3.37 (m) ⎫ |
| 3.09 (d,J = 6Hz) ⎭ 4H, |
| 3.62-4.56 (m) ⎫ |
| 3.85 (s) ⎬ 9H, |
| 3.94 (s) ⎭ |
| 6.05 (1H,dt,J = 16Hz,J = 6Hz), |
| 6.46 (1H,d,J = 16Hz), |
| 6.78-7.57 (9H,m), |
| 8.40 (1H,dd,J = 5Hz,J = 2Hz) |

EXAMPLE 3

(1) 2.09 g of (E)-(4-methoxy-3-nitrophenyl)allyl alcohol was dissolved in 21 ml of methylene chloride. To the solution was added 1.79 g of thionyl chloride with ice-cooling. The mixture was stirred for 1 hour at room temperature. The solvent was removed by distillation under reduced pressure to obtain crystals of (E)-3-(4-methoxy-3-nitrophenyl)allyl chloride. The crystals were dissolved in 10 ml of methylene chloride.

(2) In 30 ml of methylene chloride were dissolved 2.02 g of triethylamine and 3.47 g of 5-(piperazin-1-yl)-10,11-dihydro-5H-benzo[4,5]cyclohepta[1,2-b]pyridine dihydrate. To the solution was dropwise added the solution obtained in the above (1), with ice-cooling. The mixture was stirred for 3 hours at room temperature. The reaction mixture was washed with water and a saturated aqueous sodium chloride solution in this order, and dried over anhydrous magnesium sulfate. The solvent was removed by distillation under reduced pressure. The residue was purified by a column chromatography (eluant: chloroform/methanol=30/1) to obtain 4.09 g of 5-[4-{(E)-3-(4-methoxy-3-nitrophenyl)allyl}piperazin-1-yl]-10,11-dihydro-5H-benzo[4,5]-cyclohepta[1,2-b]pyridine.

Melting point: 159°-161° C. (IPA)

IR (KBr) cm$^{-1}$: 2930, 2800, 1520, 1440, 1355, 1270, 1140, 1000, 970, 760.

| NMR (CDCl$_3$) δ value: |
|---|
| 2.38 (8H,bs), |
| 2.62-3.33 (m) ⎫ |
| 3.11 (d,J = 5Hz) ⎭ 4H, |
| 3.65-4.53 (m) ⎫ |
| 3.93 (s) ⎭ 6H, |
| 6.11 (1H,dt,J = 16Hz,J = 5Hz), |
| 6.47 (1H,d,J = 16Hz), |

| NMR (CDCl$_3$) δ value: |
|---|
| 6.87–7.53 (8H,m), |
| 7.80 (1H,d,J = 2Hz), |
| 8.40 (1H,dd,J = 5Hz,J = 2Hz) |

EXAMPLE 4

1.96 g of (E)-3-(4-methylsulfinylphenyl)allyl alcohol was dissolved in 40 ml of methylene chloride. To the solution were added 1.34 g of 4-N,N-dimethylamino)-pyridine and 2.19 g of p-toluenesulfonyl chloride with ice-cooling. The mixture was stirred for 4 hours at room temperature. To the reaction mixture were added 1.32 g of triethylamine and 3.15 g of 5-(piperazin- 1-yl)-10,11-dihydro-5H-benzo[4,5]cyclohepta[1,2-b]pyridine dihydrate. The mixture was stirred for 5 hours at room temperature. The reaction mixture was washed with water and a saturated aqueous sodium chloride solution in this order, and dried over anhydrous magnesium sulfate. The solvent was removed by distillation under reduced pressure. The residue was purified by a column chromatography (eluant: chloroform/methanol=35/1) to obtain 2.31 g of 5-[4-{(E)-3-(4-methylsulfinylphenyl)allyl}piperazin-1-yl]-10,11-dihydro-5H-benzo-[4,5]cyclohepta[1,2-b]pyridine. It was recrystallized from isopropyl alcohol to obtain 1.85 g of colorless crystals having a melting point of 166°–168° C.

IR (KBr) cm$^{-1}$: 2920, 2790, 1435, 1135, 1080, 1045, 995, 965, 775.

| NMR (CDCl$_3$) δ value: |
|---|
| 2.37 (8H,bs), |
| 2.60–3.42 (m) ⎫ |
| 2.67 (s)         ⎬ 7H, |
| 3.11 (d,J = 5Hz) ⎭ |
| 3.56–4.56 (m) ⎫ 3H, |
| 3.93 (s)          ⎭ |
| 6.26 (1H,dt,J = 16Hz,J = 5Hz), |
| 6.57 (1H,d,J = 16Hz), 6.80–7.70 (10H,m), |
| 8.39 (1H,dd,J = 5Hz,J = 2Hz) |

EXAMPLE 5

1.13 g of triphenylphosphine was added to a solution of 870 mg of (E)-3-[4-(tert-butyldimethylsilyloxymethyl)phenyl]allyl alcohol and 1.31 g of carbon tetrabromide dissolved in 9 ml of tetrahydrofuran, with ice-cooling in a nitrogen atmosphere. The mixture was stirred for 1 hour at room temperature to obtain a solution containing (E)-3-[4-(tert-butyldimethylsilyloxymethyl)phenyl]allyl bromide. To this solution was added a solution of 430 mg of triethylamine and 950 mg of 5-(piperazin-1-yl)-10,11-dihydro-5H-benzo[4,5]-cyclohepta[1,2-b]pyridine dihydrate dissolved in 10 ml of methylene chloride, with ice-cooling. The mixture was stirred for 1 hour at room temperature. The solvent was removed by distillation under reduced pressure. The residue was mixed with 20 ml of water and 30 ml of ethyl acetate. The organic layer was separated and 20 ml of water was added thereto. The mixture was adjusted to pH 1.0 with dilute hydrochloric acid. The aqueous layer was separated and 30 ml of ethyl acetate was added thereto. The mixture was adjusted to pH 9.0 with sodium carbonate. The organic layer was separated, washed with water and a saturated aqueous sodium chloride solution, and dried over anhydrous magnesium sulfate. The solvent was removed by distillation under reduced pressure. The residue was purified by a column chromatography (eluant: n-hexane/acetone=2/1) to obtain 390 mg of colorless solid 5-[4-{(E)-3-(4-hydroxymethylphenyl)allyl}piperazin-1-yl]-10,11-dihydro-5H-benzo[4,5]cyclohepta[1,2-b]pyridine.

IR (KBr) cm$^{-1}$: 3400, 2800, 1440, 1140, 1000, 760.

| NMR (CDCl$_3$) δ value: |
|---|
| 2.36 (8H,bs), |
| 2.50–3.50 (m) ⎫ |
| 3.08 (d,J = 5Hz) ⎬ 5H, |
| 3.55–4.50 (m) ⎫ 3H, |
| 3.92 (s)          ⎭ |
| 4.64 (2H,s), 6.13 (1H,dt,J = 16Hz,J = 5Hz), |
| 6.51 (1H,d,J = 16Hz), 6.76–7.64 (10H,m), |
| 8.36 (1H,dd,J = 5Hz,J = 2Hz) |

The following compounds was obtained in a similar manner.

5-[4-{(E)-3-(4-hydroxyphenyl)allyl}piperazin-1-yl]-10,11-dihydro-5H-benzo[4,5]cyclohepta-[1,2-b]pyridine
Melting point: 202°–205° C.

IR (KBr) cm$^{-1}$: 3330, 2990, 2920, 2780, 1595, 1500, 1435, 1265, 1125, 985, 815, 775.

| NMR (CDCl$_3$) δ value: |
|---|
| 2.41 (8H,bs), |
| 2.62–3.40 (m) ⎫ |
| 3.10 (d,J = 6Hz) ⎬ 4H, |
| 3.45–4.55 (m) ⎫ 3H, |
| 3.96 (s)          ⎭ |
| 5.94 (1H,dt,J = 16Hz,J = 6Hz), |
| 6.36 (1H,d,J = 16Hz), 6.40–7.65 (11H,m), |
| 8.39 (1H,dd,J = 5Hz,J = 2Hz) |

EXAMPLE 6

(1) 11.54 g of triphenylphosphine was added to a solution of 7.83 g of (E)-3-(3-triphenylmethylaminophenyl)allyl alcohol and 14.59 g of carbon tetrabromide dissolved in 60 ml of tetrahydrofuran, with ice-cooling. The mixture was stirred for 1 hour at the same temperature to obtain a tetrahydrofuran solution of (E)-(3-triphenylmethylaminophenyl)allyl bromide. To this solution were added 4.45 g of triethylamine and 6.47 g of 3-nitro-5-(piperazin-1-yl)-10,11-dihydro-5H-dibenzo[a,d]cycloheptene, with ice-cooling. The mixture was stirred for 5 hours at room temperature. To the reaction mixture was added 200 ml of water and the mixture was extracted with chloroform. The extract was washed with water and dried over anhydrous magnesium sulfate. The solvent was removed by distillation under reduced pressure. The residue was purified by a column chromatography (eluant: n-hexane/acetone=3/1) to obtain 7.8 g of light yellow oily 3-nitro-5-[4-{(E)-3-(3-triphenylmethylaminophenyl)allyl}piperazin-1-yl]-10,11-dihydro-5H-dibenzo[a,d]cycloheptene.

IR (neat) cm$^{-1}$: 3000, 2800, 1590, 1510, 1340, 1210.

(2) 7.0 g of 3-nitro-5-[4-{(E)-3-(3-triphenylmethylaminophenyl)allyl}piperazin-1-yl]-10,11-dihydro-5H-dibenzo[a,d]cycloheptene was dissolved in 20 ml of acetic acid and 20 ml of methanol. The solution was stirred for 2 hours at 40° C. The solvent was removed by distillation under reduced pressure. The residue was dissolved in 100 ml of ethyl acetate. The solution was washed with a saturated aqueous sodium hydrogen-carbonate solution, water and a saturated aqueous sodium chloride solution in this order and dried over anhydrous magnesium sulfate. The solvent was removed by distillation under reduced pressure. The residue was purified by a column chromatography (eluant: chloroform/ethanol=50/1) to obtain 3.77 g of light yellow solid 3-nitro-5-[4-{(E)-3-(3-aminophenyl)allyl}-piperazin-1-yl]-10,11-dihydro-5H-dibenzo[a,d]cycloheptene.

IR (KBr) cm$^{-1}$: 3350, 2800, 1600, 1510, 1340.

EXAMPLE 7

(1) 1.01 g of (E)-3-(1-methyl-6-indolyl)acrylic acid was suspended in 20 ml of methylene chloride. 560 mg of triethylamine was added thereto. To the mixture was dropwise added 570 mg of ethyl chlorocarbonate at −30° to −20° C. The mixture was stirred for 1 hour at the same temperature. To the reaction mixture was added 1.73 g of 5-(piperazin-1-yl)-10,11-dihydro-5H-benzo[4,5]cyclohepta[1,2-b]pyridine dihydrate. The mixture was stirred for 1 hour at room temperature. To the reaction mixture was added 20 ml of water. The organic layer was separated, washed with a saturated aqueous sodium chloride solution, and dried over anhydrous magnesium sulfate. The solvent was removed by distillation under reduced pressure. The residue was purified by a column chromatography (eluant: n-hexane/acetone=5/1) to obtain 1.73 g of 5-[4-{(E)-3-(1-methyl-6-indolyl)acryloyl}piperazin-1-yl]-10,11-dihydro-5H-benzo[4,5]cyclohepta[1,2-b]pyridine.

IR (KBr) cm$^{-1}$: 1635, 1590, 1430, 1200, 980, 800, 760.

(2) 1.73 g of the compound obtained in the above (1) was suspended in 7.3 ml of toluene. To the suspension was dropwise added 2.24 g of a 70% toluene solution of bis(2-methoxyethoxy)aluminum sodium hydride at room temperature. The mixture was stirred for 1 hour at the same temperature. To the reaction mixture was dropwise added 15 ml of water. The mixture was adjusted to pH 1.5 with dilute hydrochloric acid. The aqueous layer was separated and 20 ml of ethyl acetate was added thereto. The mixture was adjusted to pH 9 with potassium carbonate. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: n-hexane/acetone=5/1) to obtain 1.17 g of 5-[4-{(E)-3-(N-methyl-6-indolyl)allyl}piperazin-1-yl]-10,11-dihydro-5H-benzo[4,5]cyclohepta[1,2-b]pyridine.

Melting point: 168°–170° C. (acetonitrile)

IR (KBr) cm$^{-1}$: 2940, 2800, 1440, 1340, 1315, 1140, 1000, 970, 770.

EXAMPLE 8

The compounds shown in Tables 10, 11, 12, 13, 14, 15 and 16 were obtained in a manner similar to that of Example 1, 2, 3, 4, 5, 6 or 7.

TABLE 10

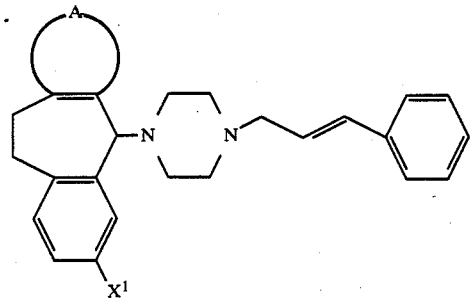

| A | X$^1$ | Melting point (°C.) | IR: cm$^{-1}$ | NMR (CDCl$_3$) δ value: |
|---|---|---|---|---|
| CH=CH—CH=H | —H | 121*$^2$~122 | (KBr) 2930, 2785, 1440, 1135, 995, 965, 745 | 2.39(8H, bs), 2.52–3.00(2H, m), 3.10(2H, d, J=5Hz), 3.58–4.32(2H, m), 4.41(1H, s), 6.18(1H, dt, J=16Hz, J=5Hz), 6.52(1H, d, J=16Hz), 6.90–7.47(11H, m), 8.28(1H, dd, J=5Hz, J=2Hz) |
| CH=N—CH=CH | —H | 129*$^4$~130 | (KBr) 2930, 2780, 1440, 1140, 1130, 1000, 970, 750 | 2.37(8H, bs), 2.63–3.15(m) } 4H, 3.10(d, J=6Hz) 3.52–4.36(m) } 3H, 3.92(s) 6.16(1H, dt, J=16Hz, J=6Hz), 6.53(1H, d, J=16Hz), 7.01–7.38(10H, m), 8.24–8.32(2H, m) |

TABLE 10-continued

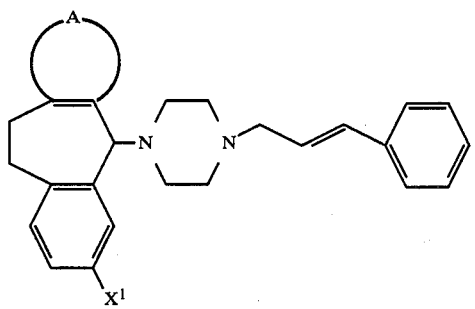

| A | $X^1$ | Melting point (°C.) | IR: cm$^{-1}$ | NMR (CDCl$_3$) δ value: |
|---|---|---|---|---|
| CH=CH—N=CH | —H | Oily | (neat) 2920, 2800, 1445, 1245, 1140, 1000, 970, 765 | 2.20–4.68(m), 2.40(bs), 3.12(d, J=5Hz), 4.04(s) } 15H, 6.17(1H, dt, J=16Hz, J=5Hz), 6.54(1H, d, J=16Hz), 6.84–7.68(10H, m), 8.33(1H, d, J=5Hz), 8.38(1H, s) |
| N=CH—CH=CH | —Me | — | (KBr) 2910, 2780, 1440, 1135, 995, 965, 740 | 2.25(3H, s), 2.45(8H, bs), 2.70–3.31(m), 3.19(d, J=6Hz) } 4H, 3.60–4.42(m), 3.92(s) } 3H, 6.20(1H, dt, J=16Hz, J=6Hz), 6.56(1H, d, J=16Hz), 6.86–7.52(10H, m), 8.39(1H, dd, J=5Hz, J=2Hz) |
| N=CH—CH=CH | —OMe | — | (KBr) 2920, 2780, 1500, 1445, 1260, 1140, 1000, 965, 745 | 2.47(8H, bs), 2.82–3.45(m), 3.20(d, J=6Hz) } 4H, 3.56–4.40(m), 3.74(s), 3.91(s) } 6H, 5.96–7.52(12H, m), 8.40(1H, dd, J=5Hz, J=2Hz) |
| N=CH—CH=CH | —NO$_2$ | — | (KBr) 2800, 1510, 1440, 1340, 1140, 1000, 750 | 2.40(8H, bs), 2.64–3.44(m), 3.12(d, J=5Hz) } 4H, 3.52–4.80(m), 4.08(s) } 3H, 6.17(1H, dt, J=16Hz, J=5Hz), 6.54(1H, d, J=16Hz), 6.80–7.68(8H, m), 7.80–8.20(2N, m), 8.44(1H, dd, J=5Hz, J=2Hz) |
| N=CH—CH=CH | —Cl | Oily | (neat) 2930, 2800, 1440, 1135, 995, 965, 755 | 2.38(8H, bs), 2.60–3.35(m), 3.11(d, J=6Hz) } 4H, 3.54–4.53(m), 3.88(s) } 3H, 6.17(1H, dt, J=16Hz, J=6Hz), 6.53(1H, d, J=16Hz), 6.86–7.56(10H, m), |

TABLE 10-continued
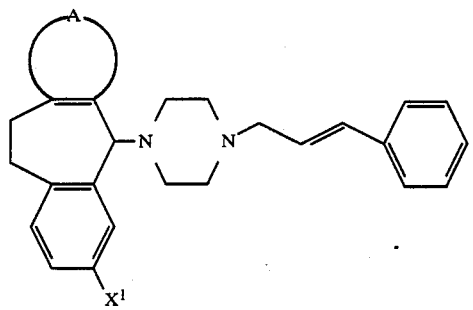
| A | X[1] | Melting point (°C.) | IR: cm[-1] | NMR (CDCl$_3$) δ value: |
|---|---|---|---|---|
| | | | | 8.42 1H, dd, J=5Hz, 2Hz) |
*[2] Recrystallized from ethyl acetate
*[4] Recrystallized from diisopropyl ether
TABLE 11
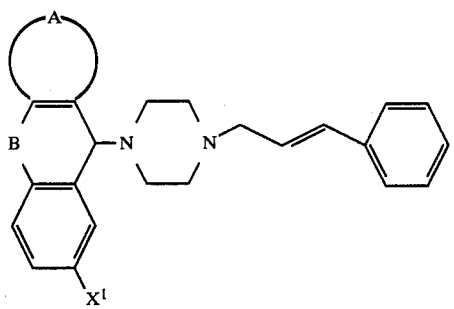
| A | B | X[1] | Melting point (°C.) | IR (KBr): cm[-1] |
|---|---|---|---|---|
| N=CH—CH=CH | [—OSi⟨] | — | | 2900, 1600, 1490, 1440, 1260, 960, 860, 780 |
| N=CH—CH=CH | [ | —NHAc | 199–202 (AcOEt) | 3280, 2790, 1660, 1590, 1535, 1495, 1440, 1135, 1000, 965, 745 |
| N=CH—CH=CH | [S | —H | 126–132 | 2920, 2780, 1440, 1140, 1000, 750 |
| N=CH—CH=CH | [O | —H | 127–129 (AcOEt) | 2930, 2800, 1480, 1445, 1220, 1140, 1000, 760 |
| N=CH—CH=CH | [ | —H | 143–144 (CH$_3$CN) | 2790, 1440, 1140, 1000, 960, 810, 740 |
| N=CH—CH=CH | [ | —Cl | 146–150 (AcOEt) | 2940, 2790, 1440, 1135, 995, 965, 840, 800, 745 |
| N=CH—CH=CH | [ | —NO$_2$ | 124–128 | 2800, 1510, 1440, 1340, 1140 |

TABLE 11-continued

[Structure: bicyclic A-B ring system connected to piperazine-cinnamyl group with X¹ substituent]

| A | B (with branch) | X¹ | Melting point (°C.) | IR (KBr): cm⁻¹ |
|---|---|---|---|---|
| CH=CH-C(NO₂)=CH | [S-containing ring] | —H | — | 2920, 2790, 1510, 1340, 1140 |
| CH=CH-C(NO₂)=CH | [O-containing ring] | —H | 184–186 (AcOEt) | 2930, 2800, 1510, 1340, 1250, 1240, 1000, 740 |
| CH=CH-CH(NO₂)=CH | [alkyl chain] | —H | 132–133 (AcOEt-n-hexane) | 2790, 1520, 1340, 1130, 995, 960, 740 |

TABLE 12

[Structure: pyrido-benzocycloheptene with piperazine linked to substituted cinnamyl group bearing R¹, R³, R⁴, R⁵]

| R¹ | R³ | R⁴ | R⁵ | Melting point (°C.) | IR: cm⁻¹ | NMR (CDCl₃) δ value: |
|---|---|---|---|---|---|---|
| —H | —OMe | —H | —H | 173*⁵~174 | (KBr) 2920, 2800, 1480, 1440, 1240, 1140, 1000, 750 | 2.39(8H, bs), 2.58–3.34(m) / 3.12(d, J=6Hz) } 4H, 3.64–4.64(m) / 3.80(s) / 3.94(s) } 6H, 6.20(1H, dt, J=16Hz, J=6Hz), 6.62–7.74(m) / 6.83(d, J=16Hz) } 11H, 8.40(1H, dd, J=5Hz, J=2Hz) |
| —H | —H | —OMe | —H | 147*⁶~151 | (KBr) 2930, 2790, 1590, 1485, 1445, 1320, 1255, 1160, 995, 970, 785 | 2.38(8H, bs), 2.60–3.38(m) / 3.11(d, J=5Hz) } 4H, 3.52–4.60(m) / 3.78(s) / 3.94(s) } 6H, 6.15(1H, dt, J=6Hz, J=5Hz), 6.52(1H, d, J=16Hz), 6.60–7.64(10H, m), |

TABLE 12-continued

| R¹ | R³ | R⁴ | R⁵ | Melting point (°C.) | IR: cm⁻¹ | NMR (CDCl₃) δ value: |
|---|---|---|---|---|---|---|
| | | | | | | 8.40(1H, dd, J=5Hz, J=2Hz) |
| —H | —H | —H | —OMe | 127*⁷~128 | (KBr) 2940, 2800, 1600, 1510, 1440, 1260, 1140, 1000, 970, 960 | 2.38(8H, bs), 2.62–3.42(m) } 4H, 3.08(d, J=6Hz) 3.62–4.62(m) 3.77(s) } 6H, 3.93(s) 6.03(1H, dt, J=16Hz, J=6Hz), 6.46(1H, d, J=16Hz), 6.74–7.74(10H, m), 8.39(1H, dd, J=5Hz, J=2Hz) |
| —H | —H | —H | —NO₂ | — | (KBr) 2920, 2800, 1590, 1510, 1440, 1340, 1140, 1000, 860 | 2.40(8H, bs), 2.60–3.50(m) } 4H, 3.17(d, J=5Hz) 3.50–4.98(m) } 3H, 3.96(s) 6.32(1H, dt, J=16Hz, J=5Hz), 6.63(1H, d, J=16Hz), 6.80–8.28(10H, m), 8.40(1H, dd, J=5Hz, J=2Hz) |
| —H | —H | —O—C₆H₅ | —OMe | — | (KBr) 2920, 2790, 1480, 1440, 1260, 1220, 1120, 1000, 750 | 2.36(8H, bs), 2.60–3.40(m) } 4H, 3.05(d, J=6Hz) 3.60–4.55(m) 3.80(s) } 6H, 3.93(s) 5.99(1H, dt, J=16Hz, J=6Hz), 6.38(1H, d, J=16Hz), 6.72–7.64(14H, m), 8.39(1H, dd, J=5Hz, J=2Hz) |
| —H | —OMe | —OMe | —OMe | 146*²~148 | (KBr) 2930, 2800, 1440, 1290, 1095, 995, 765 | 2.39(8H, bs), 2.65–3.37(m) } 4H, 3.12(d, J=6Hz) 3.64–4.56(m) 3.82(s) 3.83(s) } 12H, 3.85(s) 3.94(s) 6.11(1H, dt, J=16Hz, J=6Hz), 6.50–7.56(9H, m), 8.40(1H, dd, J=5Hz, J=2Hz) |
| —H | —H | —O—CH₂—O— (R⁴–R⁵) | | 118*⁸~119 | (KBr) 2930, 2790, 1440, 1255, 1140, 1000, 965, 780, 760 | 2.37(8H, bs), 2.62–3.36(m) } 4H, 3.07(d, J=6Hz) 3.62–4.56(m) } 3H, 3.93(s) 5.90(2H, s), |

TABLE 12-continued
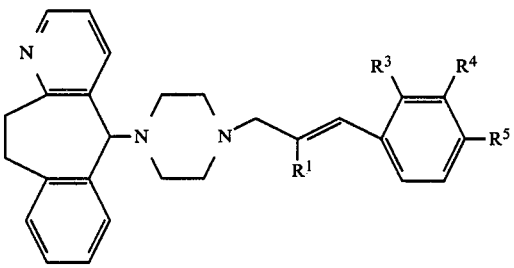
| R¹ | R³ | R⁴ | R⁵ | Melting point (°C.) | IR: cm⁻¹ | NMR (CDCl₃) δ value: |
|---|---|---|---|---|---|---|
| | | | | | | 6.01(1H, dt, J=16Hz, J=6Hz), 6.42(1H, d, J=16Hz), 6.63–7.56(9H, m), 8.40(1H, dd, J=5Hz, J=2Hz) |
| —Me | —H | —H | —H | — | (KBr) 2800, 1440, 1135, 1000, 740, 695 | 1.86(3H, d, J=1Hz), 2.34(8H, bs), 2.60–3.56(m) / 2.94(bs) } 4H, 3.60–4.60(m) / 3.93(s) } 3H, 6.37(1H, bs), 6.70–7.60(11H, m), 8.39(1H, dd, J=5Hz, J=2Hz) |
| —Br | —H | —H | —H | — | (KBr) 2925, 2800, 1445, 1140, 1000, 760, 690 | 2.40(8H, bs), 2.66–3.33(m) / 3.32(d, J=1Hz) } 4H, 3.66–4.53(m) / 3.95(s) } 3H, 6.87–7.66(12H, m), 8.40(1H, dd, J=5Hz, J=2Hz) |
| —H | —H | —H | —SMe | 153*⁶~154 | (KBr) 2920, 2790, 1490, 1440, 1140, 1000, 970, 785, 765 | 2.37(bs) / 2.44(s) } 11H, 2.62–3.40(m) / 3.09(d, J=5Hz) } 4H, 3.52–4.56(m) / 3.93(s) } 3H, 6.12(1H, dt, J=16Hz, J=5Hz), 6.47(1H, d, J=16Hz), 6.74–7.58(10H, m), 8.40(1H, dd, J=5Hz, J=2Hz) |
| —H | —H | —H | —SO₂Me | 157*⁶~159 | (KBr) 2930, 2790, 1435, 1305, 1145, 1085, 995, 960, 765 | 2.39(8H, bs), 2.70–3.38(m) / 3.01(s) / 3.14(d, J=5Hz) } 7H, 3.58–4.56(m) / 3.95(s) } 3H, 6.31(1H, dt, J=16Hz, J=5Hz), 6.62(1H, d, J=16Hz), 6.80–7.64(m) / 7.48(d, J=8Hz) } 8H, 7.86(2H, d, J=8Hz), 8.40(1H, dd, J=5Hz, J=2Hz) |

TABLE 12-continued

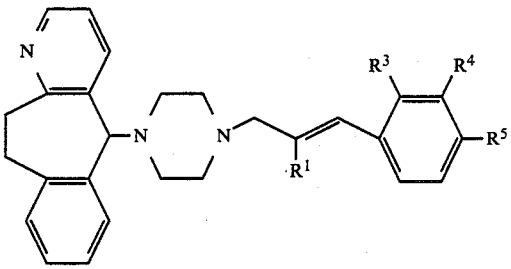

| $R^1$ | $R^3$ | $R^4$ | $R^5$ | Melting point (°C.) | IR: cm$^{-1}$ | NMR (CDCl$_3$) δ value: |
|---|---|---|---|---|---|---|
| —H | —H | —H | —CH=CH$_2$ | 136*5~137 | (KBr) 2925, 2780, 1440, 1320, 1140, 970, 910, 850, 760 | 2.38(8H, bs), 2.60–3.40(m) ⎫ 3.10(d, J=5Hz) ⎬ 4H, 3.60–4.60(m) ⎫ 3.93(s) ⎬ 3H, 5.19(1H, dd, J=11Hz, J=1Hz), 5.67(1H, dd, J=18Hz, J=1Hz), 6.16(1H, dt, J=16Hz, J=5Hz), 6.51(1H, d, J=16Hz), 6.69(1H, dd, J=16Hz), J=11Hz), 6.80–7.60(10H, m), 8.40(1H, dd, J=5Hz, J=2Hz) |

*[2]Recrystallized from ethyl acetate
*[5]Recrystallized from isopropyl alcohol
[6]Recrystallized from ethanol
*[7]Recrystallized from acetone-diisopropyl ether
*[8]Recrystallized from diethyl ether

TABLE 13

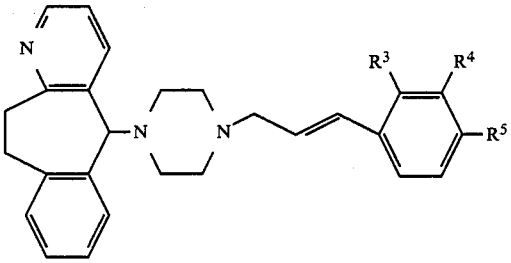

| $R^3$ | $R^4$ | $R^5$ | Melting point (°C.) | IR: cm$^{-1}$ | NMR (CDCl$_3$) δ value: |
|---|---|---|---|---|---|
| —Cl | —H | —H | 128*6~130 | (KBr) 2930, 2780, 1560, 1440, 1315, 1260, 1140, 1000, 965, 765, 755 | 2.39(8H, bs), 2.70–3.38(m) ⎫ 3.15(d, J=6Hz) ⎬ 4H, 3.56–4.56(m) ⎫ 3.94(s) ⎬ 3H, 6.18(1H, dt, J=16Hz, J=6Hz), 6.64–7.64(11H, m), 8.39(1H, dd, J=5Hz, J=2Hz) |

TABLE 13-continued

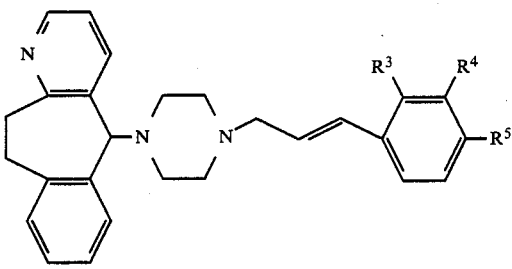

| $R^3$ | $R^4$ | $R^5$ | Melting point (°C.) | IR: cm$^{-1}$ | NMR (CDCl$_3$) δ value: |
|---|---|---|---|---|---|
| —H | —Cl | —H | Oily | (neat) 2920, 2790, 1585, 1560, 1440, 1140, 1000, 965, 760 | 2.42(8H, bs),<br>2.64–3.48(m) ⎱4H,<br>3.15(d, J=5Hz) ⎰<br>3.52–4.64(m) ⎱3H,<br>3.96(s) ⎰<br>6.18(1H, dt, J=16Hz, J=5Hz),<br>6.50(1H, d, J=16Hz),<br>6.84–7.60(10H, m),<br>8.40(1H, dd, J=5Hz, J=2Hz) |
| —H | —H | —Cl | Oily | (neat) 2925, 2800, 1485, 1420, 1140, 1090, 1000, 970, 756 | 2.45(8H, bs),<br>2.66–3.48(m) ⎱4H,<br>3.17(d, J=5Hz) ⎰<br>3.50–4.44(m) ⎱3H,<br>3.97(s) ⎰<br>6.16(1H, dt, J=16Hz, J=5Hz),<br>6.52(1H, d, J=16Hz),<br>6.80–7.64(10H, m),<br>8.41(1H, dd, J=5Hz, J=2Hz) |
| —Cl | —H | —Cl | Oily | (neat) 2925, 2790, 1460, 1440, 1140, 1105, 995, 965, 785, 760 | 2.39(8H, bs),<br>2.62–3.38(m) ⎱4H,<br>3.13(d, J=6Hz) ⎰<br>3.62–4.56(m) ⎱3H,<br>3.94(s) ⎰<br>6.17(1H, dt, J=16Hz, J=6Hz),<br>6.82(1H, d, J=16Hz),<br>6.84–7.56(9H, m),<br>8.40(1H, dd, J=5Hz, J=2Hz) |
| —H | —Cl | —Cl | 126*5~127 | (neat) 2920, 2790, 1440, 1135, 995, 965, 715 | 2.38(8H, bs),<br>2.60–3.40(m) ⎱4H,<br>3.10(d, J=5Hz) ⎰<br>3.60–4.56(m) ⎱3H,<br>3.94(s) ⎰<br>6.14(1H, dt, J=16Hz, J=5Hz),<br>6.47(1H, d, J=16Hz),<br>6.76–7.64(9H, m),<br>8.40(1H, dd, J=5Hz, J=2Hz) |

TABLE 13-continued
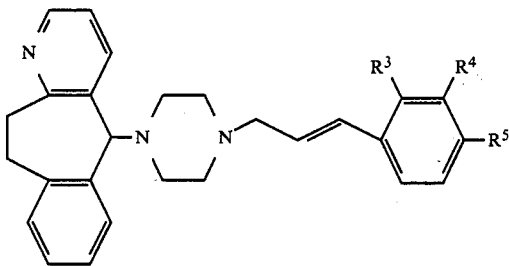
| R[3] | R[4] | R[5] | Melting point (°C.) | IR: cm[−1] | NMR (CDCl$_3$) δ value: |
|---|---|---|---|---|---|
| —H | —F | —F | Oily | (neat) 2930, 2800, 1510, 1445, 1290, 1140, 1000, 970, 765 | 2.20–2.64(8H, bs), 2.70–3.48(m) ⎫ 3.14(d, J=5Hz) ⎬4H, 3.52–4.76(m) ⎫ 3.96(s) ⎬3H, 6.11(1H, dt, J=16Hz, J=5Hz), 6.48(1H, d, J=16Hz), 6.70–7.64(9H, m), 8.14(1H, dd, J=5Hz, J=2Hz) |
| —H | —CF$_3$ | —H | Oily | (neat) 2920, 2780, 1440, 1325, 1160, 1125, 995, 965, 775 | 2.41(8H, bs), 2.64–3.38(m) ⎫ 3.14(d, J=5Hz) ⎬4H, 3.63–4.54(m) ⎫ 3.95(s) ⎬3H, 6.25(1H, dt, J=16Hz, J=5Hz), 6.58(1H, d, J=16Hz), 6.84–7.64(10H, m), 8.40(1H, dd, J=5Hz, J=2Hz) |
| —H | —CN | —H | — | (KBr) 2920, 2750, 2225, 1440, 1135, 995, 960, 760 | 2.38(8H, bs), 2.63–3.36(m) ⎫ 3.12(d, J=5Hz) ⎬4H, 3.61–4.54(m) ⎫ 3.94(s) ⎬3H, 6.22(1H, dt, J=16Hz, J=5Hz), 6.53(1H, d, J=16Hz), 6.85–7.64(10H, m), 8.40(1H, dd, J=5Hz, J=2Hz) |
| —Me | —H | —H | 150[*2]~151 | (KBr) 2930, 2780, 1480, 1440, 1135, 1000, 965, 740 | 2.30(s) ⎫ 2.39(bs) ⎬11H, 2.65–3.34(m) ⎫ 3.13(d, J=6Hz) ⎬4H, 3.66–4.55(m) ⎫ 3.94(s) ⎬3H, 6.06(1H, dt, J=16Hz, J=6Hz), 6.70(1H, d, J=16Hz), 6.86–7.56(10H, m), 8.40(1H, dd, J=5Hz, J=2Hz) |

TABLE 13-continued

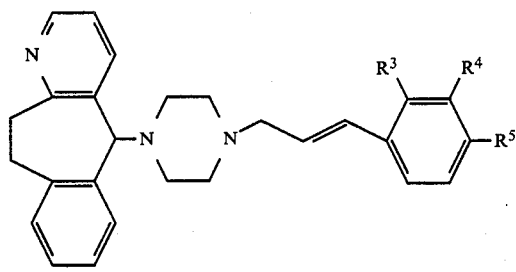

| $R^3$ | $R^4$ | $R^5$ | Melting point (°C.) | IR: cm$^{-1}$ | NMR (CDCl$_3$) δ value: |
|---|---|---|---|---|---|
| —H | —Me | —H | 112[*2]~114 | (KBr) 2930, 2790, 1440, 1145, 1130, 995, 970, 780, 770 | 2.30(s)  ⎱11H, 2.37(bs) ⎰<br>2.63–3.36(m) ⎱4H, 3.09(d, J=5Hz) ⎰<br>3.62–4.55(m) ⎱3H, 3.93(s) ⎰<br>6.15(1H, dt, J=16Hz, J=5Hz),<br>6.50(1H, d, J=16Hz),<br>6.83–7.56(10H, m),<br>8.40(1H, dd, J=5Hz, J=2Hz) |
| —H | —H | —Me | 127[*2]~129 | (KBr) 2930, 2790, 1440, 1135, 995, 965, 780, 760 | 2.30(s)  ⎱11H, 2.37(bs) ⎰<br>2.61–3.37(m) ⎱4H, 3.09(d, J=5Hz) ⎰<br>3.62–4.57(m) ⎱3H, 3.93(s) ⎰<br>6.12(1H, dt, J=16Hz, J=5Hz),<br>6.49(1H, d, J=16Hz),<br>6.83–7.55(10H, m),<br>8.40(1H, dd, J=5Hz, J=2Hz) |
| —H | —H | i-Pr | 129[*8]~130 | (KBr) 2945, 2800, 1445, 1140, 995, 965, 765 | 1.22(6H, d, J=7Hz)<br>2.37(8H, bs),<br>2.61–3.36(m) ⎱5H, 3.09(d, J=6Hz) ⎰<br>3.61–4.56(m) ⎱3H, 3.93(s) ⎰<br>6.12(1H, dt, J=16Hz, J=6Hz),<br>6.50(1H, d, J=16Hz),<br>6.83–7.56(10H, m),<br>8.40(1H, dd, J=5Hz, J=2Hz) |
| —H | —NO$_2$ | —H | Oily | (neat) 2930, 2800, 1520, 1440, 1350, 1135, 995, 735 | 2.40(8H, bs),<br>2.66–3.36(m) ⎱4H, 3.15(d, J=5Hz) ⎰<br>3.66–4.54(m) ⎱3H, 3.95(s) ⎰<br>6.34(1H, dt, J=16Hz, J=5Hz),<br>6.66(1H, d, J=16Hz),<br>6.84–7.64(8H, m),<br>7.96–8.28(2H, m),<br>8.40(1H, dd, J=5Hz, J=2Hz) |

TABLE 13-continued
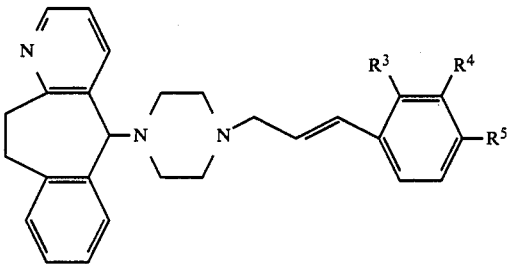
| R³ | R⁴ | R⁵ | Melting point (°C.) | IR: cm⁻¹ | NMR (CDCl₃) δ value: |
|---|---|---|---|---|---|
| —H | —H | 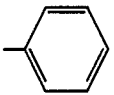 | 155*⁹~156 | (KBr) 2930, 2800, 1480, 1440, 1140, 1000, 970, 760 | 2.39(8H, bs), 2.66-3.34(m) ⎫ 3.12(d, J=6Hz) ⎬4H, 3.65-4.52(m) ⎫3H, 3.94(s) ⎬ 6.21(1H, dt, J=16Hz, J=6Hz), 6.57(1H, d, J=16Hz), 6.86-7.67(15H, m), 8.40(1H, dd, J=5Hz, J=2Hz) |
| —H | 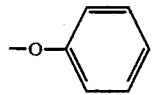 | —H | Oily | (neat) 2920, 2780, 1480, 1440, 1240, 1135, 995, 965, 755 | 2.37(8H, bs), 2.63-3.36(m) ⎫ 3.08(d, J=6Hz) ⎬4H, 3.63-4.55(m) ⎫3H, 3.93(s) ⎬ 6.13(1H, dt, J=16Hz, J=6Hz), 6.49(1H, d, J=16Hz), 6.72-7.55(15H, m), 8.40(1H, dd, J=5Hz, J=2Hz) |
| —H | —CONH₂ | —OMe | — | (KBr) 3480, 2920, 2800, 1660, 1580, 1490, 1440, 1250, 1140, 1000, 970, 760 | 2.43(8H, bs), 2.74-3.47(m) ⎫ 3.15(d, J=6Hz) ⎬4H, 3.63-4.50(m) ⎫6H, 3.93(s) ⎬ 6.14(1H, dt, J=15Hz, J=6Hz), 6.52(1H, d, J=15Hz), 6.83-7.52(10H, m), 8.18(1H, d, J=2Hz), 8.38(1H, dd, J=5Hz, J=2Hz) |
| —H | —OMe | 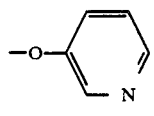 | — | (KBr) 2920, 2780, 1570, 1490, 1440, 1420, 1270, 1220, 1120, 1020, 960, 760 | 2.10-3.50(m) ⎫12H, 3.37(d, J=6Hz) ⎬ 3.60-4.64(m) ⎫ 3.80(s) ⎬6H, 4.04(s) ⎭ 6.24(1H, dt, J=16Hz, J=6Hz), 6.60(1H, d, J=16Hz), 6.80-7.62(11H, m), 8.20-8.52(3H, m) |

TABLE 13-continued

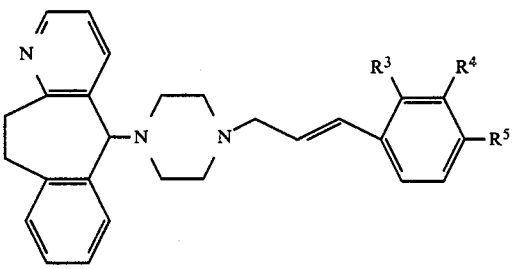

| R³ | R⁴ | R⁵ | Melting point (°C.) | IR: cm⁻¹ | NMR (CDCl₃) δ value: |
|---|---|---|---|---|---|
| —H | —O—(3-pyridyl) | —OMe | Oily | (neat) 2920, 2800, 1440, 1420, 1270, 1240, 1130, 1050, 1000, 970, 760 | 2.36(8H, bs),<br>2.60–3.40(m) ⎫<br>3.07(d, J=6Hz) ⎬4H,<br>3.60–4.60(m) ⎫<br>3.79(s) ⎬6H,<br>3.93(s) ⎭<br>6.02(1H, dt, J=16Hz, J=6Hz),<br>6.40(1H, d, J=16Hz),<br>6.70–7.60(11H, m),<br>8.20–8.50(3H, m) |

*²Recrystallized from ethyl acetate
*⁵Recrystallized from isopropyl alcohol
*⁶Recrystallized from ethanol
*⁸Recrystallized from diethyl ether
*⁹Recrystallized from diisopropyl ether-ethyl acetate

TABLE 14

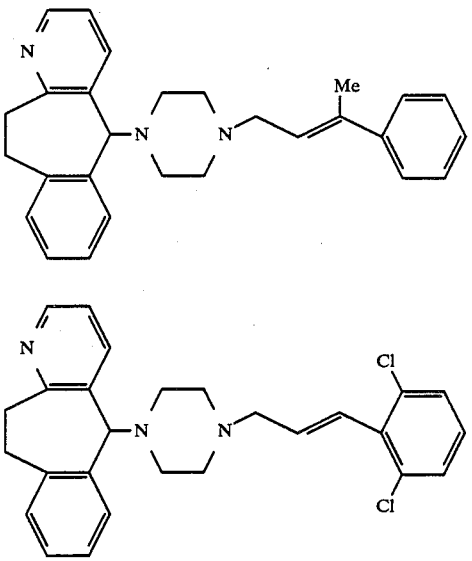

| Structure | Melting point (°C.) | IR: cm⁻¹ | NMR (CDCl₃) δ value: |
|---|---|---|---|
| (first compound) | 122*¹⁰~123 | (KBr) 2920, 2775, 1560, 1485, 1440, 1315, 1260, 1140, 1000, 840, 765, 755 | 2.02(3H, s), 2.39(8H, bs),<br>2.66–3.34(m) ⎫<br>3.13(d, J = 6Hz) ⎬4H,<br>3.64–4.52(m) ⎫<br>3.94(s) ⎬3H,<br>5.84(1H, t, J = 6Hz),<br>6.86–7.54(11H, m),<br>8.38(1H, dd, J = 5Hz, J = 2Hz) |
| (second compound) | 148*²~150 | (KBr) 2900, 2800, 1440, 1140, 995, 970, 765 | 2.16–2.64(8H, m),<br>2.66–3.37(m) ⎫<br>3.19(d, J = 5Hz) ⎬4H,<br>3.64–4.56(m) ⎫<br>3.95(s) ⎬3H,<br>6.16(1H, dt, J = 16Hz, J = 5Hz),<br>6.54(1H, d, J = 16Hz),<br>6.84–7.56(9H, m),<br>8.41(1H, dd, J = 5Hz, J = 2Hz) |

*² Recrystallized from ethyl acetate
*¹⁰ Recrystallized from isopropyl alcohol-diisopropyl ether

TABLE 15
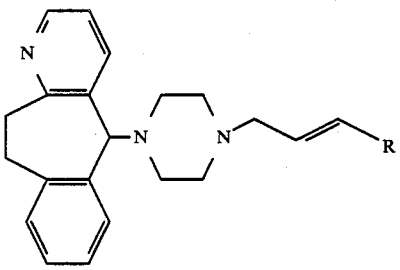
| R | Melting point (°C.) | IR (KBr): cm$^{-1}$ | R | Melting point (°C.) | IR (KBr): cm$^{-1}$ |
|---|---|---|---|---|---|
| benzofuran-yl | 156–159 (IPA) | 2925, 2780, 1440, 1130, 995, 970, 780, 740 | 1,4-benzodioxin-yl | 198–200 (EtOH) | 2930, 2780, 1465, 1445, 1280, 1255, 1140, 1000, 975 |
| 1,3-benzodioxol-yl | 177–179 (EtOH) | 2930, 2790, 1140, 1245, 1140, 1130, 1050, 995, 970, 935, 770, 730 | benzofurazan-yl | 163–165 (EtOH) | 2920, 2800, 1440, 1140, 990, 970 |
| 2-methylbenzothiazol-yl | Oily | (neat) 2920, 2800, 1440, 1140, 1000, 970 | 4-methylnaphth-yl | — | 2920, 2800, 1440, 1140, 1000, 810 |
| 3-(O-i-Pr)phenyl | — | 2920, 2800, 1440, 1260, 1135, 1110, 1000, 760 | 3-(O-t-Bu)phenyl | — | 2925, 2800, 1590, 1560, 1440, 1140, 1000, 760 |
| 3-Cl-4-i-Pr-phenyl | — | 2950, 2790, 1440, 1135, 995, 965, 760 | benzothiophen-yl | 183–185 (Decomposed) (AcOEt) | 2930, 2780, 1440, 1140, 1000, 970, 760 |
| 2-methylbenzothiazol-yl | 172–173 (EtOH) | 2920, 2780, 1440, 1140, 1000, 800 | 2,1,3-benzothiadiazol-yl | — | 3340, 2920, 2800, 1445, 1135, 995, 760 |

TABLE 15-continued
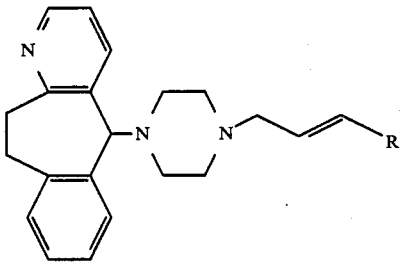
| R | Melting point (°C.) | IR (KBr): cm⁻¹ | R | Melting point (°C.) | IR (KBr): cm⁻¹ |
|---|---|---|---|---|---|
| 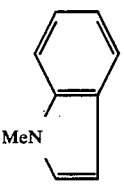 | 157–159 (AcOEt) | 2910, 2790, 1440, 1135, 995, 965, 735 | | | |
| 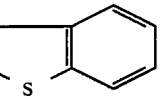 | 137–138 (Aceto-nitrile) | 2925, 2790, 1440, 1140, 990, 955, 850, 750 | 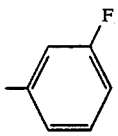 | 109–112 (n-Hexane) | 2925, 2800, 1580, 1440, 1260, 1140, 990, 970, 775 |
| 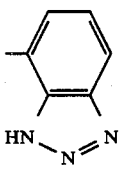 | — | 3340, 2920, 2800 1445, 1135, 995, 760 | 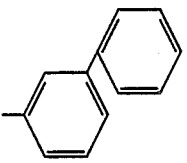 | — | 2925, 2800, 1440, 1140, 1000, 960, 760 |
| 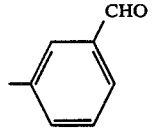 | — | 2925, 2800, 1690, 1440, 1140, 1000, 760 | 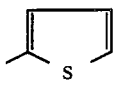 | Oily | (neat) 2920, 2800, 1440, 1135, 995, 960, 750 |
| 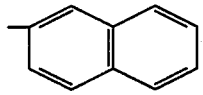 | 140–141 (AcOEt) | 2780, 1440, 1145, 1125, 1000, 970 | 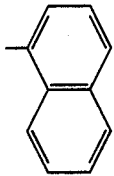 | 184–187 (Decomposed) (EtOH—CHCl₃) | 2930, 2780, 1440, 1120, 1000, 965, 780, 765 |
| 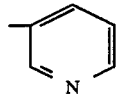 | Oily | (neat) 2925, 2800, 1440, 1215, 1135, 995, 965, 760 | 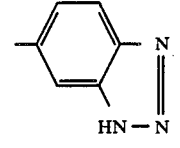 | — | 3400, 2900, 2800, 1440, 1140, 1000, 760 |
| 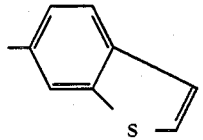 | 114–115 (AcOEt) | 2930, 2790, 1440, 1145, 1130, 995, 970, 820, 785, 770 | 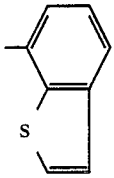 | 156–160 (AcOEt) | 2770, 1440, 1135, 995, 965 |

TABLE 15-continued
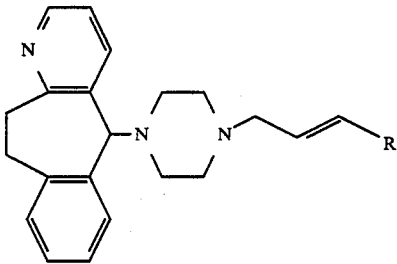
| R | Melting point (°C.) | IR (KBr): cm$^{-1}$ | R | Melting point (°C.) | IR (KBr): cm$^{-1}$ |
|---|---|---|---|---|---|
| 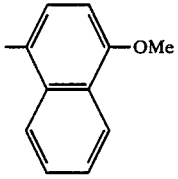 | — | 2925, 2790, 1580, 1440, 1265, 1135, 1090, 995, 965, 760 | 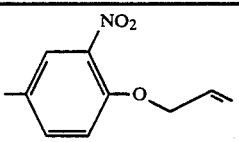 | — | 2920, 2790, 1610, 1520, 1440, 1350, 1260, 1135, 995, |
| 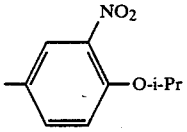 | — | 2925, 2790, 1520, 1440, 1350, 1270, 1135, 1105, 1000 | 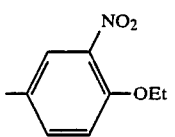 | — | 2920, 2790, 1610, 1525, 1440, 1350, 1260, 1135, 995, 965, 755 |
| 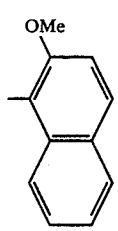 | — | 2920, 2800, 1580, 1440, 1250, 1140, 780, 760 | 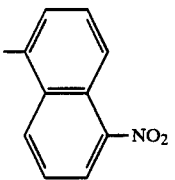 | — | 2920, 2800, 1520, 1440, 1330, 1140, 1000, 780 |
| 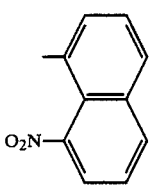 | — | 2920, 2790, 1520, 1440, 1360, 1140, 1000, 760 | 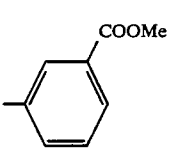 | 120–122 (Aceto-nitrile) | 2925, 2800, 1720, 1440, 1280, 1200, 1000, 970, 760 |
| 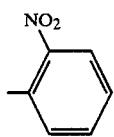 | — | 2900, 2780, 1510, 1440, 1340, 1140, 1000, 960, 860, 740 | 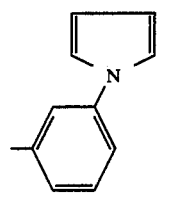 | — | 2900, 2800, 1490, 1440, 1330, 1140, 1000, 730 |
| 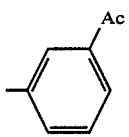 | Oily | (neat) 2930, 2800, 1680, 1440, 1350, 1280, 1140, 1000 | 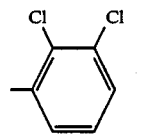 | 154–155 (IPA) | 2945, 2790, 1440, 1135, 995, 970, 760 |
| 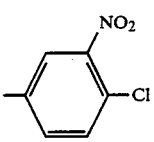 | 145–146 | 2900, 2800, 1520, 1440, 1345, 1130, 1000, 970 | 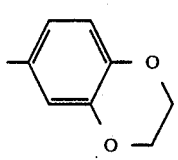 | — | 2910, 2780, 1570, 1495, 1435, 1280, 1060, 995, 965, 760 |

TABLE 15-continued

[Structure: tricyclic pyridine-benzazepine connected to piperazine-N-CH2-CH=CH-R]

| R | Melting point (°C.) | IR (KBr): cm⁻¹ | R | Melting point (°C.) | IR (KBr): cm⁻¹ |
|---|---|---|---|---|---|
| 2-NO₂-6-i-Pr-phenyl | Oily | (neat) 2930, 2800, 1520, 1440, 1350, 1135, 995, 965, 755 | benzofuran-2-yl | 119–121 (AcOEt-IPE) | 2920, 2780, 1440, 1260, 1120, 1000, 970, 760 |
| benzo[b]thiophen-2-yl | 157–159 (AcOEt) | 2920, 2800, 1440, 1330, 1140, 1000, 970 | furan-2-yl | Oily | (neat) 2920, 2900, 1440, 1140, 1000, 965, 760 |
| benzo[b]thiophen-3-yl | 182–184 (Benzene) | 2925, 2780, 1440, 1140, 1000, 965, 760, 730 | 4-OMe-3-NO₂-phenyl (shown as 2-OMe-5-NO₂) | 182–183 (EtOH) | 2930, 2800, 1580, 1510, 1440, 1340, 1260, 1140 |
| 2-NO₂-3-OMe-phenyl | — | 2920, 2790, 1520, 1440, 1360, 1270, 1135, 995, 965, 850, 760 | 2-(1,2,3-thiadiazol-yl)phenyl | 174–175 (AcOEt) | 2920, 2780, 1440, 1290, 1130, 990, 950 |
| phenyl | 130–131 (EtOH—H₂O) | 2930, 2780, 1440, 1133, 995, 965, 745 | 3,4-di-OMe-phenyl | 135–136 (AcOEt-n-hexane) | 2910, 2785, 1440, 1265, 1135, 1020, 995, 965, 765 |
| 2-NO₂-4-OMe-phenyl | 159–161 (IPA) | 2930, 2800, 1520, 1440, 1355, 1270, 1140, 1000, 970, 760 | 4-S(O)Me-phenyl | 166–168 (IPA) | 2920, 2790, 1435, 1135, 1080, 1045, 995, 965, 775 |
| 4-CH₂OH-phenyl | — | 3400, 2800, 1440, 1140, 1000, 760 | 4-OH-phenyl | 202–205 | 3330, 2990, 2920, 2780, 1595, 1500, 1435, 1265, 1125, 985, 815, 775 |
| 1-methylindol-3-yl | 168–170 (Acetonitrile) | 3400, 2800, 1440, 1340, 1315, 1140, 1000, 970, 770 | 1-phenyl-2-oxopyrrolidin-yl | — | 2925, 2800, 1690, 1440, 1320, 1140, 1000 |

TABLE 16
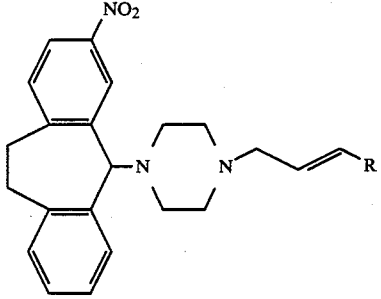
| R | Melting point (°C.) | IR (KBr): cm⁻¹ | R | Melting point (°C.) | IR (KBr): cm⁻¹ |
|---|---|---|---|---|---|
| 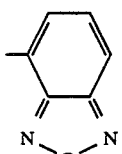 | — | 2925, 2800, 1510, 1340, 1140, 1000, 750 | 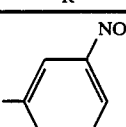 | — | 2900, 2780, 1510, 1340, 730 |
| 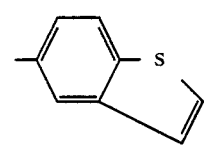 | 172–173 (Dioxane) | 2925, 2790, 1510, 1340 | 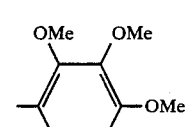 | Oily | (neat) 2925, 1515, 1485, 1450, 1340, 1290, 1090, 780, 760 |
| 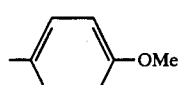 | 147–151 (AcOEt) | 2910, 2775, 1600, 1505, 1340, 1240, 1135 | 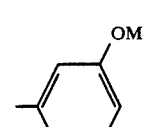 | 129–130 (AcOEt) | 2920, 2780, 1580, 1515, 1340 |
| 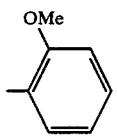 | 180–181 (Dioxane) | 2925, 2790, 1510, 1440, 1335, 1235, 1130, 995, 970, 750 | 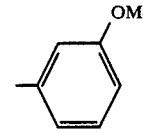 | — | 2925, 2800, 1515, 1340, 1140, 1000, 730 |
| 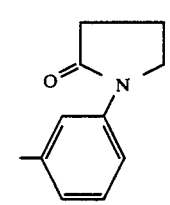 | — | 2940, 2800, 1690, 1515, 1340, 1140, 1000, 780 | 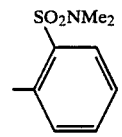 | 171–173 (AcOEt) | 2930, 2800, 1515, 1450, 1340, 1160, 1000, 955, 750 |
| 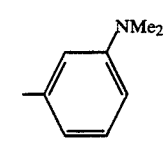 | Oily | (neat) 2925, 2790, 1590, 1515, 1340, 1140, 1000, 970, 785, 760 | 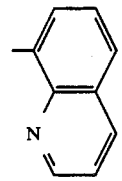 | — | 2925, 2790, 1515, 1440, 1130, 1000, 800 |
| 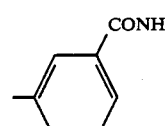 | — | 3300, 2780, 1650, 1500, 1440, 1130, 995, 960, 740 | 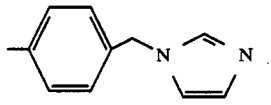 | — | 2925, 2800, 1510, 1340, 1140, 750 |

TABLE 16-continued

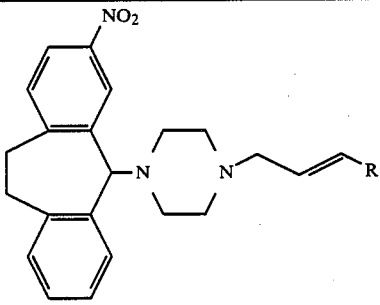

| R | Melting point (°C.) | IR (KBr): cm$^{-1}$ | R | Melting point (°C.) | IR (KBr): cm$^{-1}$ |
|---|---|---|---|---|---|
| 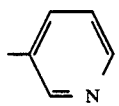 | 135–139 (AcOEt) | 2930, 2790, 1515, 1340, 1140, 995, 970, 760 | 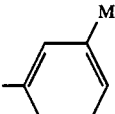 | 138–139 (AcOEt) | 2925, 2780, 1515, 1340, 1140, 995, 970, 855, 765 |
| 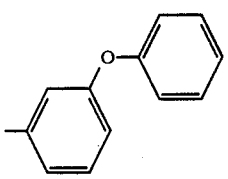 | — | 2920, 2790, 1515, 1480, 1345, 1240, 1140 | 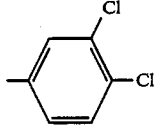 | 128–132 (AcOEt-IPE) | 2920, 2780, 1510, 1330, 1120 |
| 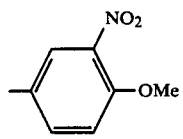 | — | 2920, 2790, 1520, 1345, 1270 | 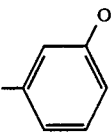 | 108–109 | 3400, 2800, 1510, 1340, 1130, 970, 770 |
| 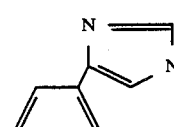 | — | 3050, 2920, 2800, 1510, 1340, 1130, 760 | 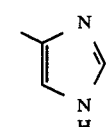 | 135–136 (AcOEt) | 2930, 2800, 1515, 1340, 1130, 1000, 965 |
| 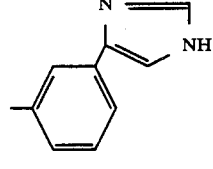 | — | 3350, 2800, 1600, 1510, 1340 | 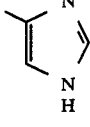 | — | 3350, 2925, 2800, 1520, 1340, 1140, 1000, 970 |

EXAMPLE 9

3.29 g of 5-[4-{(E)-3-(4-methoxy-3-nitrophenyl)allyl}piperazin-1-yl]-10,11-dihydro-5H-benzo[4,5]cyclohepta[1,2-b]pyridine was dissolved in 40 ml of 80% ethanol. 3.91 g of an iron powder and 0.7 ml of 1N hydrochloric acid were added thereto. The mixture was stirred for 3 hours at 50° C. The reaction mixture was cooled to room temperature and neutralized with a 10% aqueous sodium hydroxide solution. To the resulting mixture was added 65 ml of chloroform and 20 ml of water. The resulting insolubles were removed by filtration. An organic layer was separated from the filtrate, washed with water, and dried over anhydrous magnesium sulfate. The solvent was removed by distillation under reduced pressure. The residue was purified by a column chromatography (eluant: chloroform/methanol=30/1) to obtain 2.47 g of light yellow solid 5-[4-{(E)-3-(3-amino-4-methoxyphenyl)allyl}piperazin-1-yl]-10,11-dihydro-5H-benzo[4,5]cyclohepta[1,2-b]pyridine.

IR (KBr) cm $^{-1}$: 3450, 3350, 2920, 2780, 1500, 1435, 1230, 1130, 995, 960, 780, 760.

| NMR (CDCl$_3$) δ value: |
|---|
| 2.37(8H, bs), |
| 2.66–3.34(m)  ⎫ |
| 3.07(d, J = 6Hz)  ⎬ 4H, |
| 3.62–4.52(m) |
| 3.70(bs)  ⎫ |
| 3.82(s)  ⎬ 8H, |
| 3.93(s) |
| 5.97(1H, dt, J = 16Hz, J = 6Hz), |

-continued

| NMR (CDCl₃) δ value: |
|---|
| 6.37(1H, d, J = 16Hz), 6.69–7.25(8H, m), |
| 7.45(1H, dd, J = 7Hz, J = 2Hz), |
| 8.38(1H, dd, J = 5Hz, J = 2Hz) |

EXAMPLE 10

In 22 ml of pyridine was dissolved 2.20 g of 5-[4-{(E)-3-(3-amino-4-methoxyphenyl)allyl}piperazin-1-yl]-10,11-dihydro-5H-benzo[4,5]cyclohepta[1,2-b]pyridine. To the solution was added 690 mg of methanesulfonyl chloride with ice-cooling. The mixture was stirred for 30 minutes at the same temperature. The solvent was removed by distillation under reduced pressure. The residue was purified by a column chromatography (eluant: chloroform/methanol=50/1) to obtain 920 mg of colorless solid 5-[4-{(E)-3-methylsulfonylamino-4-methoxyphenyl)allyl}piperazin-1-yl]-10,11-dihydro-5H-benzo[4,5]cyclohepta[1,2-b]pyridine.

IR (KBr) cm⁻¹: 3350, 2910, 2800, 1500, 1440, 1260, 1150, 1120, 995, 965, 780, 760.

| NMR (CDCl₃) δ value: |
|---|
| 2.39(8H, bs), |
| 2.66–3.34(m) ⎫ |
| 2.93(s)           ⎬  7H, |
| 3.10(d, J = 5Hz) ⎭ |
| 3.65–4.51(m) ⎫ |
| 3.87(s)           ⎬  6H, |
| 3.95(s)           ⎭ |
| 6.09(1H, dt, J = 16Hz, J = 5Hz), |
| 6.47(1H, d, J = 16Hz), 6.75–7.54(1H, m), |
| 8.40(1H, dd, J = 5Hz, J = 2Hz) |

The following compound was obtained in a similar manner.

3-Nitro-5-[4-{(E)-3-(3-methylsulfonylaminophenyl)allyl}piperazin-1-yl]-10,11-dihydro-5H-dibenzo[a,d]cycloheptene IR (KBr) cm⁻¹: 2800, 1600, 1580, 1510, 1340, 1150, 970.

EXAMPLE 11

In 20 ml of ethanol was dissolved 1.05 g of 5-[4-{(E)-3-phenylallyl}piperazin-1-yl]-7-tert-butyldimethylsilyloxy-10,11-dihydro-5H-benzo[4,5]cyclohepta[1,2-b]pyridine. The solution was adjusted to pH 0.5 with 6 N hydrochloric acid and then stirred for 12 hours at room temperature. The reaction mixture was adjusted to pH 8.0 with a 10% aqueous sodium hydroxide solution. The solvent was removed by distillation under reduced pressure. To the residue were added 20 ml of water and 20 ml of ethyl acetate. The organic layer was separated, washed with water and a saturated aqueous sodium chloride solution in this order, and dried over anhydrous magnesium sulfate. The solvent was removed by distillation under reduced pressure. The residue was purified by a column chromatography (eluant: n-hexane/acetone=2/1) to obtain 600 mg of 5-[4-{(E)-3-phenylallyl}piperazin-1-yl]-7-hydroxy-10,11-dihydro-5H-benzo[4,5]cyclohepta[1,2-b]pyridine. It was recrystallized from ethanol to obtain 510 mg of colorless crystals having a melting point of 136°–140° C.

IR (KBr) cm⁻¹: 3000, 2900, 2800, 1440, 1270, 1130, 990, 960, 860, 740.

EXAMPLE 12

In 20 ml of ethanol was dissolved 2.27 g of 5-[4-{(E)-3-(3-methoxycarbonylphenyl)allyl}piperazin-1-yl]-10,11-dihydro-5H-benzo[4,5]cyclohepta[1,2-b]pyridine. 320 mg of sodium hydroxide was added thereto. The mixture was refluxed for 1 hour. The solvent was removed by distillation under reduced pressure. To the residue was added 15 ml of water and 10 ml of diethyl ether. The mixture was adjusted to pH 7.0 with dilute hydrochloric acid. The resulting crystals were collected by filtration and dried to obtain 1.62 g of colorless crystals of 5-[4-{(E)-3-(3-carboxyphenyl)allyl}piperazin-1-yl]-10,11-dihydro-5H-benzo[4,5]cyclohepta[1,2-b]pyridine having a melting point of 144° C. (decomposed).

IR (KBr) cm⁻¹: 3400, 2900, 2800, 1700, 1560, 1440, 1380, 970, 760.

EXAMPLE 13

In 12 ml of ethanol was dissolved 2.26 g of 7-acetylamino-5-[4-{(E)-3-phenylallyl}piperazin-1-yl]-10,11-dihydro-5H-benzo[4,5]cyclohepta[1,2-b]pyridine. 12 ml of a 50% aqueous potassium hydroxide solution was added thereto. The mixture was refluxed for 12 hours. The solvent was removed by distillation under reduced pressure. To the residue was added 30 ml of water. The mixture was extracted with chloroform. The extract was washed with water and a saturated aqueous sodium chloride solution in this order and then dried over anhydrous magnesium sulfate. The solvent was removed by distillation under reduced pressure. The residue was purified by a column chromatography (eluant: chloroform/methanol=40/1) to obtain 1.64 g of colorless solid 7-amino-5-[4-{(E)-3-phenylallyl}piperazin-1-yl]-10,11-dihydro-5H-benzo[4,5]cyclohepta[1,2-b]pyridine.

IR (KBr) cm⁻¹: 2920, 2790, 1610, 1440, 1135, 1000, 965, 745.

PREPARATION EXAMPLE 1

Tablets containing 10 mg per tablet of 5-[4-{(E)-3-(3,4-dichlorophenyl)allyl}piperazin-1-yl]-10,11-dihydro-5H-benzo[4,5]cyclohepta[1,2-b]pyridine were produced in a manner known per se using the following additives (binder solvent: H₂O):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 2

Tablets containing 10 mg per tablet of 5-[4-{(E)-3-(2,3-dichlorophenyl)allyl}piperazin-1-yl]-10,11-dihydro-5H-benzo[4,5]cyclohepta[1,2-b]pyridine were produced in a manner known per se using the following additives (binder solvent: H₂O):

| Per 10,000 tablets | |
|---|---|
| The above compound | 100 g |
| Cellulose | 250 g |

-continued

| Per 10,000 tablets | |
|---|---|
| Lactose | 300 g |
| Corn starch | 300 g |
| Hydroxypropylcellulose | 40 g |
| Magnesium stearate | 10 g |
| | 1000 g |

PREPARATION EXAMPLE 3

Tablets containing 10 mg per tablet of 5-[4-{(E)-3-(3-methoxy-4-nitrophenyl)allyl}piperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 4

Tablets containing 10 mg per tablet of 5-[4-{(E)-3-(3-nitrophenyl)allyl}piperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 5

Tablets containing 10 mg per tablet of 5-[4-{(E)-3-(3,4-dimethoxyphenyl)allyl}piperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 6

Tablets containing 10 mg per tablet of 5-[4-{(E)-3-(5-nitro-1-naphthyl)allyl}peperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 7

Tablets containing 10 mg per tablet of 5-[4-{(E)-3-(5-benzothienyl)allyl}piperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 8

Tablets containing 10 mg per tablet of 5-[4-{(E)-3-(7-benzothienyl)allyl}piperazin-1-yl]-10,11 -dihydro-5H-benzo[4,5]cyclohepta[1,2-b]pyridine were produced in a manner known per se using the following additives (binder solvent: $H_2O$):

| Per 10,000 tablets | |
|---|---|
| The above compound | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 9

Tablets containing 10 mg per tablet of 5-[4-{(E)-3-(8-nitro-1-naphthylallyl}piperazin-1-yl]-10,11-dihydro-5H-benzo[4,5]cyclohepta[1,2-b]pyridine were produced in a manner known per se using the following additives (binder solvent: $H_2O$):

| Per 10,000 tablets | |
|---|---|
| The above compund | 100 g |
| Cellulose | 250 g |
| Lactose | 300 g |
| Corn starch | 300 g |
| Hydroxypropylcellulose | 40 g |
| Magnesium stearate | 10 g |
| | 1000 g |

PREPARATION EXAMPLE 10

Fine granules containing 1% of 5-[4-{(E)-3-(3,4-dichlorophenyl)allyl}piperazin-1-yl]-10,11-dihydro-5H-benzo[4,5]cyclophepta[1,2-b]pyridine were produced in a manner known per se using the following additives (binder solvent: H₂O):

| Per 10,000 tablets | |
|---|---|
| The above compound | 10 g |
| α-Starch | 240 g |
| Purified sucrose | 250 g |
| Lactose | 470 g |
| Polyvinylpyrroldione K-90 | 30 g |
| | 1000 g |

What is claimed is:

1. A piperazine derivative represented by the following formula or a pharmaceutically acceptable salt thereof:

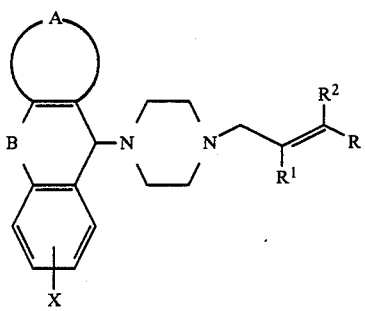

wherein A and the two carbon atoms to which A attaches form a pyridine ring or form a benzene ring substituted by a nitro group, X represents a hydrogen atom, a halogen atom, a lower alkyl group, a protected or unprotected hydroxyl group, a lower alkoxy group, a protected or unprotected amino group or a nitro group, B represents a group of the formula —CH₂CH₂— or —CH=CH— or a group of the formula —CH₂O— or —CH₂S—, either of which can be in either orientation, R¹ represents a hydrogen atom, a halogen atom, a nitro group or a lower alkyl group, R² represents a hydrogen atom, a halogen atom or a lower alkyl group, R represents an aryl group or a 5- or 6-membered heterocyclic group selected from the group consisting of an unsubstituted or oxo group-substituted pyrrolidinyl or morpholinyl group, thienyl, furyl, pyrrolyl, thiazolyl, oxazolyl, thiadiazolyl, oxadiazolyl, imidazolyl, pyridyl, or a fused heterocyclic group selected from the group consisting of a benzothienyl, benzofuranyl, indolyl, benzimidazolyl, benzotriazolyl, benzothiazolyl, benzoxazolyl, benzothiadiazolyl, bezoxadiazolyl, quinolyl, phthalazyl, benzdioxanyl group, each of which may optionally be substituted by at least one substituent selected from the group consisting of a halogen atom, a protected or unprotected hydroxyl group, a nitro group, a protected or unprotected amino group, a di-(lower alkyl)amino group, a protected or unprotected carboxyl group, a cyano group, a lower alkenyl group, a lower carboxylic acyl group, an aryl group, a lower alkenyloxy group, an aryloxy group, a heterocyclic group selected from the above recited 5- or 6-membered heterocylic group, or fused heterocyclic group a heterocyclic—O— group in which the heterocyclic group is selected from the above recited 5- or 6-membered heterocyclic group, or fused heterocyclic group a lower alkoxy group, a lower alkylthio group, a lower alkylsulfinyl group, a lower alkylsulfonyl qroup, a lower alkylsulfonylamino group, a lower alkylenedioxy group or a substituted or unsubstituted carbamoyl, sulfamoyl or lower alkyl group.

2. A piperazine derivative or a pharmaceutically acceptable salt thereof according to claim 1, wherein A and the two carbon atoms to which A attaches form a pyridine ring.

3. A piperazine derivative of a pharmaceutically acceptable salt thereof according to claim 1 or 2, wherein X represents a hydrogen atom.

4. A piperazine derivative or a pharmaceutically acceptable salt thereof according to any one of claims 1 to 3, wherein B represents a group of the formula —CH₂CH₂—.

5. A piperazine derivative or a pharmaceutically acceptable salt thereof according to any one of claims 1 to 4, wherein R¹ represents a hydrogen atom.

6. A piperazine derivative or a pharmaceutically acceptable salt thereof according to any one of claims 1 to 5, wherein R² represents a hydrogen atom.

7. A piperazine derivative or a pharmaceutically acceptable salt thereof according to claim 1, wherein A and the two carbon atoms to which A attaches from a pyridine ring, X represents a hydrogen atom, a halogen atom, a lower alkyl group, a hydroxyl group, a lower alkoxy group, an amino group or a nitro group, B represents a group of the formula —CH₂CH₂—, R¹ represents a hydrogen atom, a halogen atom, a nitro group or a lower alkyl group, R² represents a hydrogen atom or a lower alkyl group, R represents a phenyl group which may be substituted by at least one substituent selected from the group consisting of a halogen atom, a hydroxyl group, a nitro group, an amino group, a carboxyl group, a cyano group, a lower alkenyl group, a lower carboxylic acyl group, an aryl group, an aryloxy group, a heterocyclic group selected from the 5- or 6-membered heterocyclic group or fused heterocyclic group as defined in claim 1, a heterocyclic—O— group in which the heterocyclic group is selected from the 5- or 6-membered heterocyclic group or fused heterocyclic group as defined in claim 1, a lower alkoxy group, a lower alkoxycarbonyl group, a lower alkylthio group, a lower alkylsulfinyl group, a lower alkylsulfonyl group, a lower alkylsulfonylamino group, a lower alkylenedioxy group, a carbamoyl group, or a substituted or unsubstituted lower alkyl group, or a substituted or unsubstituted lower alkyl group.

8. A piperazine derivative or a pharmaceutically acceptable salt thereof according to claim 7, wherein X represents a hydrogen atom.

9. A piperazine derivative or a pharmaceutically acceptable salt thereof according to claim 7 or 8, wherein R¹ represents a hydrogen atom.

10. A piperazine derivative or a pharmaceutically acceptable salt thereof according to any one of claims 7 to 9, wherein R² represents a hydrogen atom.

11. 5-[4-{(E)-3-(3,4-dichlorophenyl)allyl}piperazin-1-yl]-10,11-dihydro-5H-benzo[4,5]cyclohepta[1,2-b]pyridine or a pharmaceutically acceptable salt thereof.

12. 5-[4-{(E)-3-(2,3-dichlorophenyl)allyl}piperazin-1-yl]-10,11-dihydro-5H-benzo[4,5]cyclohepta[1,2-b]pyridine or a pharmaceutically acceptable salt thereof.

13. 5-[4-{(E)-3-(4-methoxy-3-nitrophenyl)allyl}piperazin-1-yl]-10,11-dihydro-5H-benzo[4,5]cyclohepta[1,2-b]pyridine or a pharmaceutically acceptable salt thereof.

14. 5-[4-{(E)-3-(3-nitrophenyl)allyl}piperazin-1-yl]-10,11-dihydro-5H-benzo[4,5]cyclohepta[1,2-b]pyridine or a pharmaceutically acceptable salt thereof.

15. 5-[4-{(E)-3-(3,4-dimethoxyphenyl)allyl}piperazin-1-yl]-10,11-dihydro-5H-benzo[4,5]cyclohepta[1,2-b]pyridine or a pharmaceutically acceptable salt thereof.

16. 5-[4-{(E)-3-(5-nitro-1-naphthyl)allyl}piperazin-1-yl]-10,11-dihydro-5H-benzo[4,5]cyclohepta[1,2-b]pyridine or a pharmaceutically acceptable salt thereof.

17. 5-[4-{(E)-3-(5-benzothienyl)allyl}piperazin-1-yl]-10,11-dihydro-5H-benzo[4,5]cyclohepta[1,2-b]pyridine or a pharmaceutically acceptable salt thereof.

18. 5-[4-{(E)-3-(7-benzothienyl)allyl}piperazin-1-yl]-10,11-dihydro-5H-benzo[4,5]cyclohepta[1,2-b]pyridine or a pharmaceutically acceptable salt thereof.

19. 5-[4-{(E)-3-(8-nitro-1-naphthyl)allyl}piperazin-1-yl]-10,11-dihydro-5H-benzo[4,5]cyclohepta[1,2-b]pyridine or a pharmaceutically acceptable salt thereof.

20. 5-[4-{(E)-3-(2-chlorophenyl)allyl}piperazin-1-yl]-10,11-dihydro-5H-benzo[4,5]cyclohepta[1,2-b]pyridine or a pharmaceutically acceptable salt thereof.

21. 5-[4-{(E)-3-(3-chlorophenyl)allyl}piperazin-1-yl]-10,11-dihydro-5H-benzo[4,5]cyclohepta[1,2-b]pyridine or a pharmaceutically acceptable salt thereof.

22. 5-[4-{(E)-3-(4-chlorophenyl)allyl}piperazin-1-yl]-10,11-dihydro-5H-benzo[4,5]cyclohepta[1,2-b]pyridine or a pharmaceutically acceptable salt thereof.

23. 7-chloro-5-[4-{(E)-3-phenylallyl}piperazin-1-yl]-10,11-dihydro-5H-benzo[4,5]cyclohepta[1,2-b]pyridine or a pharmaceutically acceptable salt thereof.

24. A pharmaceutical composition comprising a piperazine derivative or a pharmaceutically acceptable salt thereof according to any one of claims 1 to 19 and 20 to 23 in an amount effective to treat a mammal having cerebrovascular disease or post-cerebrovascular disease.

25. A method of treating a mammal having cerebrovascular disease or post-cerebro-vascular disease by using an effective amount of a piperazine derivative or a pharmaceutically acceptable salt thereof according to any one of claims 1 to 19 and 20 to 23.

* * * * *